US008541188B2

(12) United States Patent
Yoon et al.

(10) Patent No.: US 8,541,188 B2
(45) Date of Patent: Sep. 24, 2013

(54) DIFFERENTIAL IMMUNOASSAY FOR PRRS VACCINE ANTIBODY

(75) Inventors: Kyoung-Jin Yoon, Ames, IA (US); Wai-Hong Wu, Ellicott City, MD (US)

(73) Assignee: Iowa State University Research Foundation, Inc., Ames, IA (US)

( * ) Notice: Subject to any disclaimer, the term of this patent is extended or adjusted under 35 U.S.C. 154(b) by 57 days.

(21) Appl. No.: 13/298,776

(22) Filed: Nov. 17, 2011

(65) Prior Publication Data

US 2012/0058466 A1 Mar. 8, 2012

Related U.S. Application Data

(63) Continuation of application No. 12/095,618, filed as application No. PCT/US2006/061487 on Dec. 1, 2006, now abandoned.

(60) Provisional application No. 60/742,095, filed on Dec. 2, 2005.

(51) Int. Cl.
*G01N 33/53* (2006.01)
*G01N 33/532* (2006.01)
*G01N 33/533* (2006.01)
*G01N 33/534* (2006.01)
*G01N 33/535* (2006.01)
*G01N 33/536* (2006.01)

(52) U.S. Cl.
USPC .............................. 435/7.92; 435/7.1; 435/7.9

(58) Field of Classification Search
None
See application file for complete search history.

(56) References Cited

U.S. PATENT DOCUMENTS

| | | | |
|---|---|---|---|
| 5,620,691 | A | 4/1997 | Wensvoort et al. |
| 6,197,310 | B1 | 3/2001 | Wensvoort et al. |
| 6,455,245 | B1 | 9/2002 | Wensvoort et al. |
| 6,495,138 | B1 | 12/2002 | van Nieuwstadt et al. |
| 6,806,086 | B2 | 10/2004 | Wensvoort et al. |
| 7,335,473 | B2 | 2/2008 | Wensvoort et al. |
| 2004/0132014 | A1 | 7/2004 | Wensvoort et al. |
| 2005/0058655 | A1 | 3/2005 | Wensvoort et al. |

OTHER PUBLICATIONS

Oleksiewicz et al. Discriminating between serological response to European-genotype live vaccine and European-genotype field strains of porcine reproductive and respiratory syndrome virus (PRRSV) by peptide ELISA. Journal of Virological Methods, 2005, vol. 129, 134-144.*
Meulenberg et al., Virology, 1996, vol. 225, pp. 44-51.
Nelson et al., Journal of Clinical Microbiology, 1993, vol. 31, No. 12, pp. 3184-3189.
Oleksiewicz, Martin B., et al., "Discriminating between serological responses to European-genotype live vaccine and European-genotype field strains of porcine reproduction and respiratory syndrome virus (PRRSV) by peptide ELISA", J. of Virological Methods 129:134-144 (2005).
Wu, Wai-Hong, et al., Dissertation Abstracts International, 2002, vol. 63, No. 5B, pp. 2200.
Wu, Wai-Hong, et al., "A 10-kDa Structural Protein of Porcine Reproductive and Respiratory Syndrome Virus Encoded by ORF2b", Virology 287:183-191 (2001).
Wu, Wai-Hong et al., "The 2b protein as a minor structural component of PRRSV", Virus Research, available online at www.sciencedirect.com (Aug. 10, 2005).
Wu, Wai-Hong, "Porcine reproductive and respiratory syndrome virus (PRRSV) protein expression studies", Thesis—Biological Sciences, South Dakota State University, 2002, Chapters 1-7, pp. 1-243. (File saved in multiple parts due to size; file 1 of 5).
Wu, Wai-Hong, Thesis, Chapter 3 Figures (File 2 of 5).
Wu, Wai-Hong, Thesis, Chapter 4 Figures (File 3 of 5).
Wu, Wai-Hong, Thesis, Chapter 5 Figures (File 4 of 5).
Wu, Wai-Hong, Thesis, Chapter 6 Figures (File 5 of 5).

* cited by examiner

*Primary Examiner* — Louise Humphrey
*Assistant Examiner* — Yun Mei
(74) *Attorney, Agent, or Firm* — McKee, Voorhees & Sease, P.L.C.

(57) ABSTRACT

The present invention relates to immunoassays for serologically differentiating animals naturally infected with PRRS virus from animals vaccinated against PRRS. The immunoassays provide detection of at least a portion of the N terminal region of the 2b portion of PRRSV. The immunoassay is preferably an enzyme-linked immunosorbent assay (ELISA).

9 Claims, 10 Drawing Sheets

```
E1    MGSMQSLFDKIG(+)              +++   SEQ ID:14
E1a    GSMQSLFDKIG                 +++   SEQ ID:15
E1b     SMQSLFDKIG                 +++   SEQ ID:16
E1c      MQSLFDKIG                 +++   SEQ ID:17
E1d       QSLFDKIG                 +++   SEQ ID:18
E1e        SLFDKIG                  -    SEQ ID:19
E2         LFDKIGQLFVDA(+)         +++   SEQ ID:20
E2a        LFDKIGQLFVD             ++    SEQ ID:21
E2b        LFDKIGQLFV               -    SEQ ID:22
E2c        LFDKIGQLF                -    SEQ ID:23
E2d        LFDKIGQL                 ?    SEQ ID:24
E2e        LFDKIGQ                  ?    SEQ ID:25
E2f         FDKIGQLFVDA             -    SEQ ID:26
E2g          DKIGQLFVDA             -    SEQ ID:27
E2h           KIGQLFVDA             ?    SEQ ID:28
E2i            IGQLFVDA             -    SEQ ID:29
E2j             GQLFVDA             -    SEQ ID:30
E3               QLFVDAFTEFLV(+)   ++    SEQ ID:31
E3a              QLFVDAFTEFL       ++    SEQ ID:32
E3b              QLFVDAFTEF        ++    SEQ ID:33
E3c              QLFVDAFTE          -    SEQ ID:34
E3d              QLFVDAFT           -    SEQ ID:35
E3e              QLFVDAF            -    SEQ ID:36
E12               G                       -
```

*Fig. 1A*

```
              10        20        30        40        50        60        70
            ....|....|....|....|....|....|....|....|....|....|....|....|....|....|....
C15(ORF2).seq  MGSMQSLFYKIGQLFVDAFTEFLVSIVDIIIFLAILYGFTIAGWLVVFCIRLVCSAILRTRSAIRSEQLQKIL*SEQ ID:39
C14(ORF2).seq  ............................................................................*
C13(ORF2).seq  ............................................................................*
C12(ORF2).seq  ............................................................................*
C11(ORF2).seq  ............................................................................*
C10(ORF2).seq  ............................................................................*
C9(ORF2).seq   ............................................................................*
C8(ORF2).seq   ............................................................................*
C7(ORF2).seq   ............................................................................*
C6(ORF2).seq   ............................................................................*
C5(ORF2).seq   ............................................................................*
C4(ORF2).seq   ............................................................................*
C3(ORF2).seq   ............................................................................*
C2(ORF2).seq   ............................................................................*
C1(ORF2).seq   ............................................................................*
1A15(ORF2).seq ............................................................................*
1A14(ORF2).seq ............................................................................*
1A13(ORF2).seq ............................................................................*
1A12(ORF2).seq ............................................................................*
1A11(ORF2).seq ............................................................................*
1A10(ORF2).seq ............................................................................*
1A9(ORF2).seq  ............................................................................*
1A8(ORF2).seq  ............................................................................*
1A7(ORF2).seq  ............................................................................*
1A6(ORF2).seq  ............................................................................*
1A5(ORF2).seq  ............................................................................*
1A4(ORF2).seq  ............................................................................*
1A3(ORF2).seq  ............................................................................*
1A2(ORF2).seq  ............................................................................*
1A1(ORF2).seq  ............................................................................*
1B15(ORF2).seq ............................................................................*
1B14(ORF2).seq ............................................................................*
1B13(ORF2).seq ............................................................................*
1B12(ORF2).seq ............................................................................*
1B11(ORF2).seq ............................................................................*
1B10(ORF2).seq ............................................................................*
1B9(ORF2).seq  ............................................................................*
1B8(ORF2).seq  ............................................................................*
1B7(ORF2).seq  ............................................................................*
1B6(ORF2).seq  ............................................................................*
1B5(ORF2).seq  ............................................................................*
1B4(ORF2).seq  ............................................................................*
1B3(ORF2).seq  ............................................................................*
1B2(ORF2).seq  ............................................................................*
1B1(ORF2).seq  ............................................................................*
1C15(ORF2).seq ............................................................................*
1C14(ORF2).seq ............................................................................*
1C13(ORF2).seq ............................................................................*
1C12(ORF2).seq ............................................................................*
1C11(ORF2).seq ............................................................................*
1C10(ORF2).seq ............................................................................*
1C9(ORF2).seq  .............................V..............................................*
1C8(ORF2).seq  ............................................................................*
1C7(ORF2).seq  ............................................................................*
1C6(ORF2).seq  ............................................................................*
1C5(ORF2).seq  ............................................................................*
1C4(ORF2).seq  ............................................................................*
1C3(ORF2).seq  ............................................................................*
1C2(ORF2).seq  ............................................................................*
1C1(ORF2).seq  ............................................................................*
3A15(ORF2).seq ........D...................................................................*
3A14(ORF2).seq ........D...................................................................*
3A13(ORF2).seq ........D...................................................................*
3A12(ORF2).seq ........D...................................................................*
3A11(ORF2).seq ........D...................................................................*
3A10(ORF2).seq ........D...................................................................*
3A9(ORF2).seq  ........D...................................................................*
```

DIFFERENTIAL IMMUNOASSAY FOR PRRS VACCINE ANTIBODY

CROSS-REFERENCE TO RELATED APPLICATIONS

This application is a Continuation Application of U.S. Ser. No. 12/095,618 filed Jul. 30, 2009, which claims priority to PCT/US2006/061487 filed Dec. 1, 2006 and U.S. Ser. No 60,742,095 filed Dec. 2, 2005, herein incorporated by reference in their entirety.

BACKGROUND OF THE INVENTION

Porcine reproductive and respiratory syndrome (PRRS), often characterized by late-term abortions and still births in sows and respiratory disease in nursery pigs, has resulted in extensive economic losses in the swine industry for over a decade. (16). First described in 1987 in the United States as "mystery swine disease", it spread rapidly, being reported in Europe in 1990 and subsequently across the world.

Porcine reproductive and respiratory syndrome virus (PRRSV), the causative agent of PRRS, is a small, enveloped, positive-stranded RNA virus consisting of eight overlapping open reading frames (ORFs). (19, 21). The virus is genetically, antigenically, and pathogenically heterogenic. (16). Substantial sequence divergence exists between the European and North American genotypes of the virus. (1, 9, 11-16, 20-21). Within each genotype, the PRRSV genomic sequences also vary significantly. (8, 13, 14, 20).

Modified live-attenuated vaccines (MLV) are currently used for the protection against PRRS mainly by providing protection against clinical disease. (18, 24). These modified live-attenuated vaccines, such as Ingelvac® PRRS MLV, have reduced the incidence and severity of PRRS outbreaks on many farms. A severe form of PRRS, designated acute or atypical PRRS, has recently been reported in the Midwestern United States. Many of these acute outbreaks occurred in PRRSV MLV-vaccinated herds, suggesting that the commonly used modified live-attenuated vaccines are not fully effective. The occurrence of the acute syndrome in vaccinated pigs resulted in the introduction of another MLV, Ingelvac® PRRS ATP, to the market in February 2000.

Other concerns about the modified live-attenuated vaccines pertain to their safety. In Danish swine herds, Ingelvac PRRS MLV vaccine virus has been shown to be capable of reverting to a pathogenic phenotype during replication in pigs. Additionally, Mengeling et al. confirmed that numerous vaccine-like field isolates, which contained the same restriction site marker that is found in the Ingelvac PRRS MLV vaccine virus, were capable of causing disease more severe than any clinical signs induced by the MLV. The restriction site marker was not identified in any isolates collected prior to the introduction of the Ingelvac PRRS MLV vaccine except for the parent strain ATCC-VR2332. Other vaccine-like strains have also been reported (9, 16, 23) and some of these isolates were shown to be mildly to moderately pathogenic in pigs. (23).

Due to the widespread use of Ingelvac® PRRS MLV and the periodic identification of vaccine-like isolates, there is a demand for a rapid assay that can be used routinely for identifying and differentiating these vaccine-like isolates from field isolates of PRRSV. Current methods for differentiating PRRSV isolates include PCR amplification, subsequent sequencing and sequence analyses, or PCR-restriction fragment length polymorphism. (27). Because these assays are costly and time-consuming, they are not very well suited for routine large-scale screening of viruses.

The heteroduplex mobility assay (HMA) is a rapid and inexpensive method of differentiating viral isolates. Delwart et al. (6) originally developed the assay for genetic typing of human immunodeficiency virus. More recently, HMA techniques have been applied to the study of other viruses such as influenza virus (29), feline immunodeficiency virus (2), measles virus (10), poliovirus (5), Newcastle disease virus (3), and hepatitis C virus (7, 28). The assay relies on the formation of mismatched base pairs when two closely related DNA molecules are combined, denatured, and reannealed. The mismatches cause structural distortions in the newly formed DNA molecule, resulting in heteroduplexes with reduced mobility on a polyacrylamide gel. It has been shown that the reduction in mobility is proportional to the degree of divergence between the two sequences. (6). The HMA, however, suffers from some of the disadvantages inherent in all screening techniques. Screening techniques assess the diversity of a sequence mixture based on indirect detection of sequence variations. Thus, these methods typically underestimate the true diversity of a sequence mixture.

As already noted, because of the high mutation rate of PRRSV and incidence of MLV vaccine revertant, a means of differentiating infected from vaccinated animals (DIVA) test would be desirable.

In furthering the industry's focus in potentially eradicating PRRS, a potential strategy involves developing marker vaccines and accompanying differential diagnostic tests. Currently, no such strategies exist in the industry for PRRS that are effective. While there is a commercial ELISA available for detecting antibody against PRRS virus, this commercial ELISA cannot differentiate vaccine-induced antibody from natural infection.

It is therefore a primary objective of the present invention to provide a more definitive strategy for PRRSV serological diagnosis.

It is a further objective of the present invention to provide a serological method of differentiating pigs naturally infected with PRRSV from animals vaccinated against PRRS.

It is still a further objective of the present invention to provide a means of differentiating pigs naturally infected with PRRSV from animals vaccinated against PRRS using the N-terminal region of 2b protein from PRRSV.

It is yet a further objective of the present invention to provide a means of differentiating pigs naturally infected with PRRSV from animals vaccinated against PRRS using an ELISA.

These and other objectives will become clear from the following detailed description of the invention.

SUMMARY OF THE INVENTION

The present invention relates to a method and means for serologically differentiating animals naturally infected with PRRS virus from animals vaccinated against PRRS. More specifically, the invention relates to a method whereby at least a portion of the N-terminal region of 2b protein in PRRSV is used as a target antigen in an immunoassay that is preferably an enzyme-linked immunosorbent assay (ELISA). A preferred embodiment of the method employs monoclonal antibodies for immunoaffinity purification of target antigens, although other purification procedures will work equally as well. Mixtures comprising purified or recombinant proteins are attached to microtiter plates or other solid supports to serve as target antigens. The invention also encompasses a monoclonal antibody assay kit for differentiating vaccinated from naturally PRRSV infected animals.

DESCRIPTION OF THE FIGURES

FIGS. 1A and 1B illustrate a detailed peptide scanning procedure for the mapping of 2b B cell epitopes.

FIG. 2 illustrates peptide sequence comparison among different PRRSV isolates.

FIG. 3 is a list of 2b protein sequences of different PRRSV isolates.

FIG. 4 is a comparison of 2b sequences from over sixty different PRRSV isolates. The bottom sequence represents the consensus sequence derived from the sequence analysis.

FIG. 5 illustrates the 2b sequence analysis of PRRSV isolated from CC-01 in vivo passage experiments. A, B and C represent different lines of in vivo passages, in which 15 different clones have been isolated from each passage.

FIG. 6 is a graph illustrating the detection of anti-2b antibodies from sera collected from MLV vaccinated pigs by indirect ELISA.

FIG. 8 is a graph illustrating the detection of anti-2b antibodies from sera collected from 13B6-infected pigs.

DETAILED DESCRIPTION OF THE INVENTION

Figure 7:
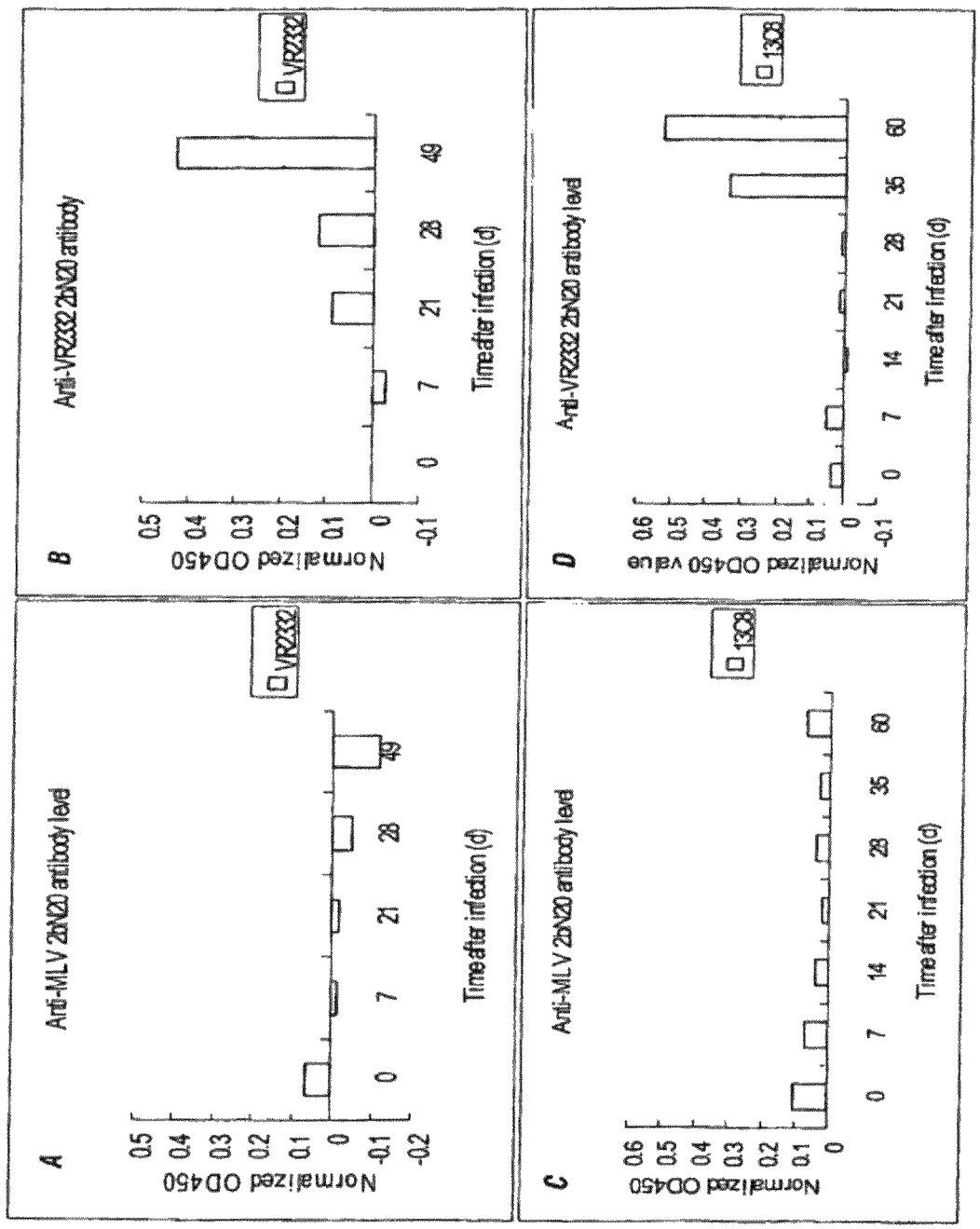
FIG. 7A-7D are graphs illustrating the detection of anti-2b antibodies from sera collected from VR2332 or 13C8-infected pigs by indirect ELISA.

The present invention relates to the identification of a 2b protein antigenic domain(s) involved in non-cross reactive humoral immunity, which can be used as a serological marker for differential diagnostic between PRRSV-vaccinated and animals naturally infected with PRRSV.

The PRRS virus 2b protein was first detected in sucrose gradient purified PRRSV virions of North American isolate SDSU-23983 (Wu et al., 2001) as a minor structural component of PRRSV (Wu et al., 2005). The 2b protein is 10 kDa in size, and encoded by mRNA2. The translation initiation site of 2b is located six nucleotides downstream of the GP2a.

The immunoassays of the present invention detect at least a portion of the N-terminal region of the 2b region of the PRRSV virus. In conducting a sequence analysis of the vaccine strain Ingelvac® PRRS MLV, it was determined that the N-terminal region of the 2b region harbors a D9Y or D9G amino acid change when compared to its parental virus, ATCC VR-2332. This 2b region tends to become antigenic after multiple passages in pigs while picking up a non-antigenic profile during serial passages in monkey kidney cell lines. The present inventors hypothesized that the "D9Y" 2b protein phenotype of Ingelvac® PRRS MLV vaccine virus may be stably maintained in immunized pigs for a certain period of time and can serve as a marker for the differentiation of natural infection caused by field isolates with different immunodominant N-terminal 2b epitopes, and this in turn could be used in preparing a successful DIVA test for PRRSV. The immunoassays of the present invention are effective in differentiating wild-type from non-wild-type PRRSV with respect to animals vaccinated with any currently available or PRRS vaccines available in the future that stably maintains the "D9Y" marker in pigs, as described herein. In this respect, the inventors are aware that at least the globally available vaccine Ingelvac® PRRS MLV includes this marker, while Ingelvac® PRRS ATP does not.

The method of differentiating animals vaccinated against PRRSV versus animals exposed to wild-type PRRSV generally involves the steps of:

(a) providing a substrate for performing a monoclonal antibody-based assay;

(b) applying to the substrate a specimen suspected of containing wild-type PRRSV;

(c) contacting the substrate with a primary monoclonal antibody for a time sufficient to allow the monoclonal antibody and an antigen of the N-terminal 2b portion of wild-type PRRSV to bind together to form an antigen-bound primary monoclonal antibody;

(d) contacting the antigen-bound primary monoclonal antibody with an anti-monoclonal antibody conjugate for a time sufficient to facilitate binding of the antigen-bound monoclonal antibody to the conjugate; and (e) applying a color reagent to the substrate, whereby the color reagent is capable of binding to the conjugate and developing a colored marking to allow visual detection of the presence of wild-type PRRSV in the specimen.

As used herein, the term "biological sample" refers to any sample suspected of containing PRRSV. The sample is typically an aqueous solution such as a body fluid from a host, for example, urine, whole blood, plasma, serum, saliva, semen, stool, sputum, cerebral spinal fluid, tears, mucus, or the like. The biological sample may also be a tissue or a tissue extract. The biological sample is preferably serum. The sample can be pretreated and can be prepared in any convenient medium that does not interfere with the assay. An aqueous medium is preferred.

As used herein, the term "conjugate" refers to a compound comprised of two or more molecules bound together, optionally through a linking group, to form a single structure. The binding can be made by a direct connection (e.g. a chemical bond) between the molecules or by use of a linking group.

As used herein, the term "hapten" refers to a compound capable of binding specifically to corresponding antibodies, but do not themselves act as immunogens (or antigens) for preparation of the antibodies. Antibodies which recognize a hapten can be prepared against compounds comprised of the hapten linked to an immunogenic (or antigenic) carrier.

As used herein, the term "immunogenic carrier" refers to a group which, when conjugated to a hapten and injected into a mammal, will induce an immune response and elicit the production of antibodies that bind to the hapten. Immunogenic carriers are also referred to as antigenic carriers. Typical immunogenic carriers include, without limitation, poly (amino acids), polysaccharides, nucleic acids and particles. Other suitable immunogenic carriers include albumins, serum proteins, e.g., globulins, ocular lens proteins and lipoproteins. Illustrative proteins include bovine serum albumin, keyhole limpet hemocyanin, egg ovalbumin, and bovine gammaglobulin.

As used herein, the term "support" or "surface" refers to a solid phase which is a porous or non-porous water insoluble material that can have any one of a number of shapes, such as strip, rod, particle or beads.

As used herein, the term "label" or "labels" include, but are not limited to, enzymes such as alkaline phosphatase, glucose-6-phosphate dehydrogenase, and horseradish peroxidase, ribozyme, a substrate for a replicase such as QB replicase, promoters, dyes, fluorescers, such as fluorescein, isothiocynate, rhodamine compounds, phycoerythrin, phycocyanin, allophycocyanin, o-phthaldehyde, and fluorescamine, chemiluminescers such as isoluminol, sensitizers, coenzymes, enzyme substrates, radiolabels, particles such as latex or carbon particles, liposomes, cells, etc. which may be further labeled with a dye, catalyst or other detectable group.

As used herein, the term "receptor" and "receptor protein" are used herein to indicate a biologically active proteinaceous molecule that specifically binds to (or with) other molecules.

As used herein, the term "ligand" refers to a molecule that contains a structural portion that is bound by specific interaction with a particular receptor protein.

As used herein, the term "antibody" refers to immunoglobulin molecules and immunologically active portions of immunoglobulin molecules, i.e., molecules that contain an antibody combining site or paratope.

As used here, the terms "monoclonal antibody" or "monoclonal antibody composition" refer to an antibody molecule that contains only one species of antibody combining site capable of immunoreacting with a particular antigen. A monoclonal antibody composition thus typically displays a single binding affinity for any antigen with which it immunoreacts. A monoclonal antibody composition is typically composed of antibodies produced by clones of a single cell called a hybridoma that secretes (produces) only one type of antibody molecule. The hybridoma cell is formed by fusing an antibody-producing cell and a myeloma or other self-perpetuating cell line. Such antibodies were first described by Kohler and Milstein, *Nature* 256:495-497 (1975), the disclosure of which is herein incorporated by reference. An exemplary hybridoma technology is described by Niman et al., *Proc. Natl. Acad. Sci. U.S.A.*, 80:4949-4953 (1983). Other methods of producing a monoclonal antibody, a hybridoma cell, or a hybridoma cell culture are also well known. See e.g., *Antibodies: A Laboratory Manual, Harlow et al.*, Cold Spring Harbor Laboratory, 1988; or the method of isolating monoclonal antibodies from an immunological repertoise as described by Sasatry, et al, *Proc. Natl. Acad. Sci. USA*, 86:5728-5732 (1989); and Huse et al., *Science*, 246:1275-1281 (1981). The references cited are hereby incorporated herein by reference.

Immunodiagnostics using specific antibodies is practical because of the sensitivity, specificity, speed, reliability and simplicity of these assays. Antibodies to modified nucleosides were first described in the 1960's (Erlanger and Beiser, 1964; Stollar, 1980), but have not gained wide popularity because of the practical difficulty in preparing high titer antibodies to 5-methylcytidine ($^{5m}$C).

The PRRS viruses to be tested include all isolates of PRRSV from any geographic location including, but not limited to, U.S., Europe, Canada, Korea, Czech Republic, etc., with North American isolates being preferred for detection in the invention. It is possible that certain non-North American PRRSV strains would include sufficient antigenic differences from the North American strains such that they would not be detectable using the methods of the invention. However, persons skilled in the art can easily test control strains of the virus prior to doing the testing to determine whether such strain would in fact be detectable using the immunoassays of the invention. Thus, it is expected that the methods of the invention will work in conjunction with viral sequences having substantial identity to North American PRRSV strains. The term "substantial identity" of sequences means that a sequence has between 50-100% polynucleotide sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90%, and most preferably at least 95%.

The sequences of PRRSV isolates are readily accessible and available from GenBank. Such isolates include, but are not limited to:

| | | | | | |
|---|---|---|---|---|---|
| VR2332 | 27011-01 | 44010-01 | 47450-01 | 16727-01 | 18571A-01 |
| 93-41462 | 19139-01 | 21373A-01 | 18087B-01 | 30603-22-01 | 12711-3-01 |
| ISU22 | PDV9502 | 98-37120-2 | 15102 44.43 | ISU1894 | 93-4506 |
| 98-27687 | 35019-01 | 18070-01 | ISU79 | ISU30262 | 89-47361 |
| 89-46489 | 89-47363 | ISU28 | 93-30352 | 1765-2-01 | ISU3927 |
| ISU33 | 92-1205 | 93-36048 | 93-45010 | ISU55 | ISU4 |
| 98-21995-1 | 98-31701 | 97-27796-4 | JA142 | 4519-01 | 97-27796-2 |
| 98-5579 | 98-4236 | VR2385 | 98-13795-3 | 98-6470 | 98-13795-1 |
| 98-13795-5 | 98-13795-10 | 98-13795-13 | SD23983 | KS1 | IAF-KLOP |
| F1 | MD001 | PA-8 | EP | AVC19381 | ONT-43697 |
| P1750-96 | DVX355 | HV-18 | PL | 93-44927 | CH-6 |
| 89-46440 | EJ-4 | | | | |

The DNA sequences of the invention can be obtained by several methods. For example, the DNA can be isolated using hybridization or computer-based techniques that are well-known in the art. Such techniques include, but are not limited to, the hybridization of genomic or cDNA libraries with probes to detect homologous nucleotide sequences; antibody screening of expression libraries to detect cloned DNA fragments with shared structural features; polymerase chain reaction (PCR) on genomic DNA or cDNA using primers capable of annealing to the DNA sequence of interest; computer searches of sequence databases for similar, sequences; and differential screening of a subtracted DNA library. The methods of this invention are designed to detect sequences of at least 10 amino acids in length, with at least 15 amino acid sequences being preferred, and about 15-20 amino acid sequences being most preferred.

Screening procedures that rely on nucleic acid hybridization make it possible to isolate any gene sequence from any organism, provided the appropriate oligonucleotide probe is available. Oligonucleotide probes, which correspond to a part of the sequences for aap or the aat gene cluster which are provided herein, can be synthesized chemically. Synthesis of other oligonucleotide probes may require that short, oligopeptide stretches of the amino acid sequence be known because the DNA sequence encoding a specific protein can be deduced using the genetic code; however, the degeneracy of the code must be taken into account. When the sequence is degenerate, it is possible to perform a mixed addition reaction that includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of MRNA sequences relating to the polypeptide of interest are present. By using stringent hybridization conditions directed to avoid non-specific binding, it is possible, for example, to allow the autoradiographic visualization of a specific cDNA or DNA clone by the hybridization of the target DNA to that single probe in the mixture that is its complete complement. (Wallace et al., Nuc. Acid Res. 9:879 (1981)). Alternatively, a subtractive library is useful for elimination of non-specific cDNA clones.

Another standard procedure for isolating DNA sequences of interest is the formation of plasmid- or phage-carrying genomic libraries which include total DNA from the organism of interest. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target DNA can be employed in DNA/DNA hybridization procedures which are carried out on cloned copies of the DNA that have been denatured into a single-stranded form. (Jay et al., Nucl. Acid Res., 11:2325 (1983).

The immunoassay tests of the present invention specifically detect at least a portion of the N-terminal region of the 2b protein associated with PRRS virus strains and, in particular, the presence or absence of the "D9Y" or "D9G" change at amino acid 9 of the N terminal region, i.e. the replacement of aspartic acid with either tyrosine or glycine. Replacement of aspartic acid at the 9th position indicates that the PRRSV is not the result of natural infection, but instead indicates the "D9Y" 2b protein phenotype of RespPRRS® vaccine virus, or virus of other PRRS vaccine that also maintains the "D9Y" 2b protein phenotype.

The antibodies of the invention may be assayed for immunospecific binding by any method known in the art. The immunoassays which can be used include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds., (1994), Current Protocols in Molecular Biology, Vol. 1, John Wiley & Sons, Inc., New York, section 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, (1994), Current Protocols in Molecular Biology, Vol. 1, John Wiley & Sons, Inc., New York, section 10.8.1.

"ELISA" refers to an enzyme-linked immunoabsorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4$^{th}$ Edition of *Basic and Clinical Immunology* by D. P. Sites et al., published by Lange Medical Publications of Los Altos, Calif. In 1982 and in U.S. Pat. Nos. 3,654,090; 3,850,752; and 4,016,043, the disclosures of which are herein incorporated by reference. ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs, the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, (1994), Current Protocols in Molecular Biology, Vol. 1, John Wiley & Sons, Inc., New York, section 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Antibodies of the invention may be characterized using immunocytochemisty methods on cells (e.g., mammalian cells, such as CHO cells) transfected with a vector enabling the expression of an antigen or with vector alone using techniques commonly known in the art. Antibodies that bind antigen transfected cells, but not vector-only transfected cells, are antigen specific.

A step in producing the assays of this invention is to collect suitable anti-PRRSV sera, which is typically produced from pooled serum and polyclonal antibodies, either concentrated or not concentrated. These antibodies are used to immunochemically detect at least one sequence of the N-terminal region of the PRRSV 2b protein. As noted above, the antibodies of this invention may also be monoclonal antibodies that contain only one species of antibody combining site capable of immunoreacting with a particular antigen.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host mediated processes.

Generally, immunogens are prepared by attaching the individual antigenic molecule onto an immunogenic carrier molecule capable of inducing antibody synthesis in animals. An immunogen is defined herein as a substance of sufficient size that when introduced into an animal stimulates the production of antibodies reactive with the specific antigen or epitope. Immunogenic carrier is defined herein as a protein or other high molecular weight compound to which an antigen or epitope is conjugated in vitro and which renders the antigen or epitope capable of stimulating or increasing an immune response. The antigens of the present invention may be synthesized using any suitable synthesis technique. Such procedures are well known to persons skilled in the art.

The antigens are covalently coupled to high molecular weight carrier proteins which include, but are not limited to, bovine serum albumin (BSA), bovine thyroglobulin (BT), keyhole limpet hemocyanin (KLH), ovalbumin (OA), and the like, with BSA and BT being preferred. The oxidized ribosides containing methylated purine derivatives are coupled to the linking amino acid, lysine, followed by borohydride reduction.

Monoclonal antibodies of the present invention can be produced using conventional methods, including by initiation of a monoclonal hybridoma culture comprising a nutrient medium containing a hybridoma that produces and secretes antibody molecules of the appropriate polypeptide specificity. The culture is maintained under conditions and for a time period sufficient for the hybridoma to secrete the antibody molecules into the medium. The antibody-containing medium is then collected. The antibody-containing medium can then be further isolated by well known techniques.

Media useful for the preparation of these compositions are both well known in the art and commercially available and include synthetic culture media, inbred mice and the like. An exemplary synthetic medium is Dulbecco's minimal essential medium (DMEM; Dulbecco et al., Virol. 8:396 (1959)) supplemented with 4.5 gm/l glucose, 20 mm glutamine, and 20% fetal calf serum. An exemplary inbred mouse strain is the BALB/c.

Immunochemical detection methods are well known to those of skill in the art and the creation of antibodies, including monoclonal antibodies, to modified nucleotides has been the subject of many publications. See, e.g. D. C. Eichler & D. G. Glitz, "Nucleotide-Specific Antibodies as Potential Blocking Agents in the Structural Analysis of Nucleic Acids", 335 BBA 303-317 (1974); C. W. Achwal and H. S. Chandra, "A sensitive immunochemical method for detecting 5 mC in DNA fragments", FEB Letters, 150:469-472 (1982); B. F. Erlanger & S. M. Beiser, "Antibodies to methylated bases in nucleic acids", Proc. Nat Acad Sciences, USA, 52:68 (1964); Brooks et al., "An improved method for the purification of IgG monoclonal antibodies from culture supernatants", Journal of Immunological Methods, 155:129-32 (1992); Sano et al., "Detection of heavy methylation in human repetitive DNA subsets by a monoclonal antibody against 5-methylcytosinen", Biochemica et Riophysica Acta., 951:157-65 (1988). A variety of non-radioactive formats are currently available including the use of infra-red tags, fluorescent dyes, chemiluminescence, and alkaline-phosphatase conjugated antibodies. A more preferred embodiment utilizes specific antibodies which can be used to immunochemically detect PRRSV 2b reaction products.

Thus, in preferred embodiments of this invention, the antibody or antigen reagent component can be affixed to a solid matrix to form a solid support that is separately packaged in the subject diagnostic systems. The reagent is typically affixed to the solid matrix by adsorption from an aqueous medium, although other modes of affixation, well known to those skilled in the art, can be used. Useful solid matrices are well known in the art. Such materials include the cross-linked dextran available under the trademark SEPHADEX from Pharmacia Fine Chemicals (Piscataway, N.J.); agarose; polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry powder, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packages discussed herein in relation to diagnostic systems are those customarily utilized in diagnostic systems. Such packages include glass and plastic (e.g., polyethylene, polypropylene and polycarbonate) bottles, vials, plastic and plastic-foil laminated envelopes and the like.

The present invention also contemplates any method that results in detecting portions of the N-terminal region of PRRSV 2b protein, in vitro or in vivo. The method for detecting the protein sequence(s) comprises the formation of an immunoreaction product between at least one PRRSV 2b protein sequence and an anti-PRRSV antibody molecule, as disclosed herein, and the subsequent detection of the immunoreaction product so formed. The PRRSV 2b protein sequence(s) to be detected can be present in a biological or vascular fluid sample, such as a blood sample, or can be present in a body tissue or tissue extract. Those skilled in the art will understand that there are numerous well known clinical diagnostic chemistry procedures that can be utilized to form detectable immunocomplexes. Thus, while exemplary assay methods are described herein, the invention is not so limited.

Various heterogeneous and homogeneous assay protocols can be employed, either competitive or non-competitive for detecting the presence and preferably amount of PRRSV 2b protein in a body sample, preferably a body fluid sample, more preferably a vascular fluid sample such as blood. The method involves the admixture of a biological sample with antibody molecules that immunoreact with one or more sequences from the PRRSV 2b protein region, but not with unbound molecules.

Biological assay conditions are those that maintain the biological activity of the antibody molecules and polypeptide molecules of this invention and the PRRSV sought to be assayed. Those conditions include a temperature range of about 4-45° C. at a pH value of 5-9, and an ionic strength varying from that of distilled water to that of about one molar sodium chloride, preferably about that of physiological saline.

The methods of this invention can be adapted to any ELISA format, for example, coating the wells with polyclonal or monoclonal antibodies from any animal species, i.e. rabbit, goat, sheep, chicken, mouse, etc. Generally, the ELISA assays of this invention first involve the preparation of a carrier protein substrate. Wells of plastic ELISA strips are then coated with the carrier protein, preferably at a concentration of 25-50 μg/ml. If present, the wild-type PRRSV in the biological sample added to the ELISA wells (or to the tube) catalyzes the formation of a reaction product. Anti-PRRSV polyclonal porcine serum then covalently binds to the reaction product, and peroxidase conjugated protein binds to the antibodies. The peroxidase conjugated protein is preferably horseradish peroxidase (HRP), but other peroxidase conjugated proteins are also appropriate for use in this invention, including but not limited to, goat anti-rabbit IgG, sheep anti-rabbit IgG, etc. The reaction product becomes colored in the presence of a peroxidase substrate, such as tetramethylbenzidine (TMB). Other appropriate peroxidase substrates include 2,2'-azinodi-(3-ethylbenzthiazoline-6-sulfonate) (ABTS) and ortho-phenylenediamine (OPD). The optical density of the chromagenic reaction product is then measured, whereby the optical density is directly proportional to the amount of 2b protein sequences present.

The following examples are offered to illustrate but not limit the invention. Thus, it is presented with the understanding that various formulation modifications as well as method of delivery modifications may be made and still are within the spirit of the invention.

EXAMPLE 1

DIVA Test for PRRSV

Materials and Methods
Viruses, Bacteria and Cells

Different strains of PRRSV which include VR2332, SD23983, MLV, JA142 and ATP were propagated in MARC-145 cells and used in these studies. MARC-145 cell culture was maintained in DMEM supplement with 10% fetal bovine serum. E. coli strain DH5 alpha and BL21 were growing in LB broth and 2×YT broth respectively.

Serum and Antibodies

Different panels of anti-PRRSV sera were used in this study. These includes anti-VR2332, SD23983, MLV, JA142, and ATP porcine sera which collected from pooled serum and polyclonal antibodies either concentrated with ammonium sulfate preparation or used as-is. Anti-GST conjugated HRP (Abcam,) with HRP, panel of porcine sera also collected from pigs experimentally infected with PRRSV in vivo.

DNA Plasmid and Protein Expression

Figure 4:
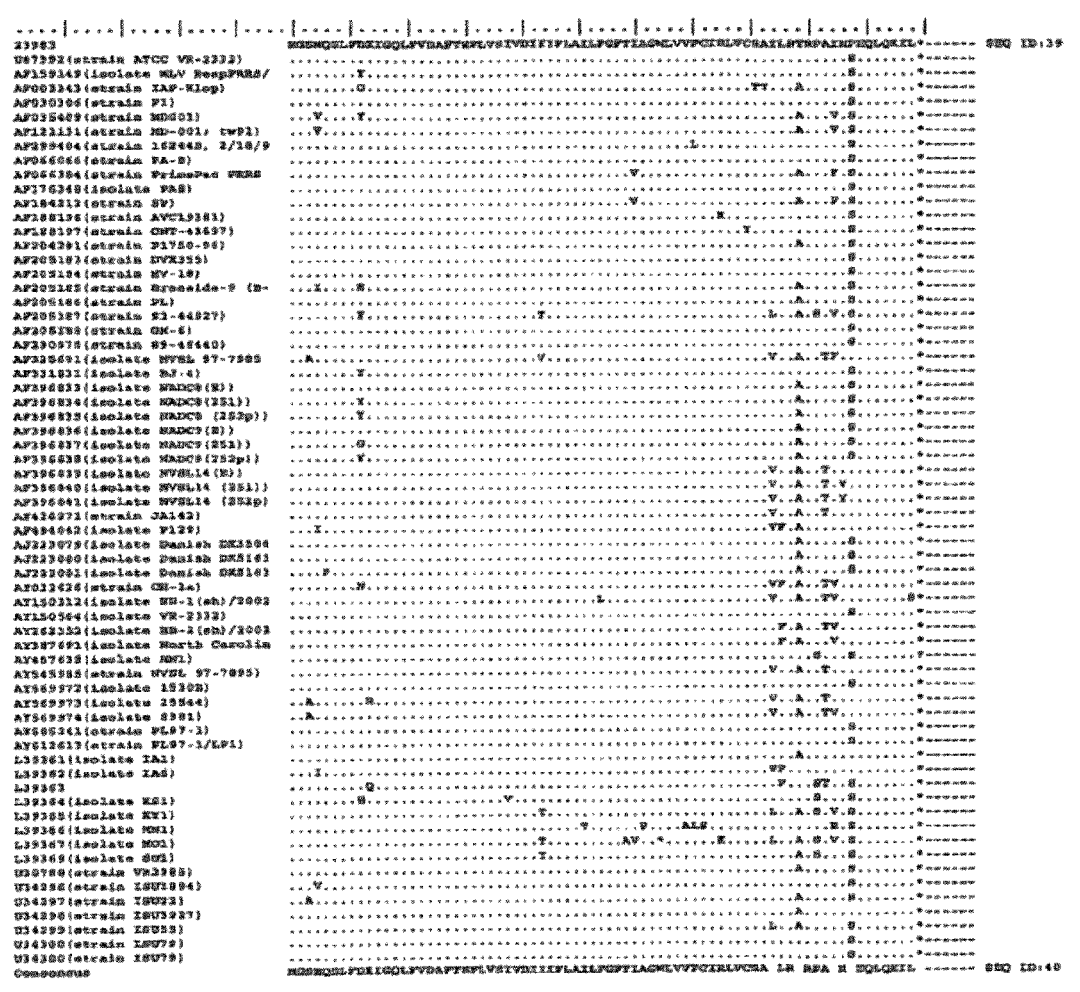

Small overlapping DNA fragments, prepared by annealing complementary oligonucleotides, were ligated in frame into pGEX6P3 (Amersham Pharmacia Biotech) and transformed into DH5α E. coli. The double-stranded DNA fragments derived from complementary oligonucleotides were designed to code the first 20 amino acid at the N terminal of different PRRSV isolates (MLV, VR2332, KS1, IAF-KLOP) or small overlapping peptides of 7-9 amino acids, which covered the region between amino acids 60 and 73 in 2b of SD23983 (FIG. 4) (SEQ ID NOS. 39-40). For expression of GST-2b peptides, the pGEX-2b peptide constructs were transformed into E. coli strain BL21 and protein production induced to high levels by the addition of isopropyl β-D-thiogalactopyranoside (IPTG). GST-2b peptides were purified on a glutathione sepharose 4B column (Amersham Pharmacia Biotech). PRRSV 2b gene fragments then encoded the 20 amino acid on the N terminal were generated by hybridization of complementary oligonucleotide and insert into the BamHI and Xho I site of plasmid pGEX-6P3. Recombinant plasmids were transformed into DH5 alpha and BL21 for plasmid DNA replication and protein expression, respectively.

Peptides Blots and Western Blot Immunoassay

Panel of overlapping peptides in 10 to 12 amino acid which cover the full length 2b protein were synthesized and dot blotted in order onto a nylon membrane. Each peptide represents 10 to 12 amino acids on the 2b sequence. Peptide blots were blocking in 5% skim milk in 1×PBS for 1 h at room temp. Blot was then stained with anti-PRRSV polyclonal porcine serums for 1 h. The filters were incubated with the appropriate antibody followed by a horseradish peroxidase-labeled secondary antibody, according to the manufacturer's instructions. Antibody binding to the filters was detected using a supersignal chemiluminescence kit (PIERCE). Proteins resolved by SDS-PAGE electrophoresis were transferred to nitrocellulose membranes (Schleicher & Schuell). Membranes were blocked in PBS containing 0.5% Tween-20 (PBST) for 45 min at room temp then incubated with a 1:100 dilution of pooled PRRSV-immune pig sera diluted in PBST and incubated for 45 min at room temperature. Bound antibodies were detected with protein G horseradish peroxidase (Sigma), diluted to a concentration of 0.2 μg/ml in PBST. After washing 3 times in PBS containing 0.05% Tween-20, peroxidase activity was detected using SuperSignal West Pico chemiluminescent substrate (Pierce Chemical) according to manufacturer's instructions using Kodak X-OMAT X-ray film.

Nucleotide and Amino Acid Sequence Analysis 2b nucleotide and amino acid sequences from SD23983 and GenBank assession Nos.

AF003343, AF046869, AF066066, AF066384, AF159149, AF176348, AF188196, AF188197, AF204291, AF205183, AF205184, AF205185, AF205186, AF205187, AF205188, AF290975, AF299404, AF299405, AF299406, AF299407, AF299408, AF299409, AF299410, AF299411, AF299412, AF299413, AF299414, AF299415, AF299416, AF299417,

AF325691, AF396833, AF396834, AF396835, AF396836, AF396837, AF396838, AF396839, AF396840, AF396841, AF396842, AF396843, AF396844, AF494042, AY150564, AY387691, AY424271, AY545985, AY569972, AY569973, AY569974, L39361, L39362, L39363, L39364, L39365, L39366, L39367, L39368, L39369, U20788, U34296, U34297, U34298, U34299, U34300, U34300 were downloaded from GenBank for the analysis. All analyses were performed using the Lasergene DNASTar program.

Purification of Recombinant Fusion Protein

Different recombinant GST-2b fusion proteins without C-terminal 6× his tags were purified by using Glutanoine-4-seprohose bead according to the suggested manufacturer manual (GST expression manual; Amersham). Recombinant GST-6× his and GST-2b N20-6× his fusion proteins were purified from frozen bacteria pellets collected from 1 liter of culture. 40 ml of ice cold column binding buffer supplemented with 0.1 mg/ml of Pefablock protease inhibitor (Roche) was added to the frozen pellets and shaking at 4° C. until the pellets were totally resuspended. Two ml of lysozyme (10 mg/ml) were then added to the pooled suspension and shaken at room temperature for 20 minutes. Later, 400 µl of 1M $MgCl_2$ was added to the suspension, along with 4 ml of Triton X-100, to reach the final concentration of $Mg^{2+}$ and Triton X-100 to 10 mM and 1% (v/v) respectively. The suspension was shaken for another 10 min at room temperature and then clarified at 27,000×g for 20 min at 4° C. Supernatant was collected and 3 ml of nickel chelated agarose (Pierce) was added and mixed overnight at 4° C. Supernatant/nickel chelated agarose mixture was loaded into a glass column and washed with 100 ml of column binding buffer containing 20 mM of imdazole. Recombinant protein was then eluted with an elution buffer (1×TBS pH 7.4 [25 mM Tris, 3 mM KCl, 140 mM NaCl]; 1% of B-Per II [Pierce] and 250 mM imdazole) and kept in 4° C. The presence of respective recombinant GST-2b fusion proteins in each preparation was confirmed by Western immunoblotting using HRP anti-GST antibody which compare to GST only show to have lower in molecular weight when migrated on a SDS-PAGE gel. Concentrations of each purified recombinant 2b proteins were determined with DC™ Protein Assay (Bio-Rad, Hercules, Calif., USA).

ELISA

An indirect ELISA was established using published standard protocol with modifications. Recombinant proteins were diluted in 0.2 M carbonate-bicarbonate coating buffer [pH 9.4]) and added into the ELISA plate (Dynex technologies; immulon II). In brief, GST2bN20 and GST were coated at a concentration of 100 ng/well and 50 µl volume per well for overnight at 4° C. Plates were washed with phosphate-buffered saline (PBS) containing 0.1% Tween 20 and blocked with 1×PBS with 10% skim milk power by incubating at 37° C. for 1 h. After blocking, plates were washed with PBST again and were ready for the binding of specific antibody from pig serum.

Serum samples used for the detection of 2b antibody is 1:100 diluted in PBS containing 0.1% Tween 20, 1% skim milk and 1% crude BL21/GST6× his bacteria cell lysates and added in duplicate into wells that were coated with GST fusion protein. The crude bacteria cell lysates were prepared by resuspending each gram of bacteria pellet in 1 ml of a Tris lysis buffer (10 mM Tris, 0.04% CHAP, 0.15M NaCl, 0.0001% aprotinin and 1 mM EDTA [pH8.0]) and incubated 2 h at 4° C. on a shaking platform. After lysis and shaking, bacteria lysates were used directly for serum dilution or kept at −80° C. until needed. After adding of diluted serum samples, ELISA plates were incubated at 37° C. for 1 h and rinsed 3 times with PBST. After washing, goat anti-swine IgG or IgM antibodies (KPL) was added and incubated at 37° C. for 1 h. Specific antigen-antibody reaction was visualized by adding TMB microwell substrate (KPL) and incubated for 15 min at ambient temperature. Colorimetric reaction was stopped by adding an equal volume of 1N HCl. Then, plates were read at wavelength of 450 nm in an ELISA plate reader.

Results

Peptide Scanning and Epitope Mapping of 2b Protein

By using overlapping peptide that blotted onto cellulose membrane detected with the polyclonal pooled anti-PRRSV field sera, B cell epitopes for 2b protein of PRRSV have been mapped. When polyclonal serum is used, continuous and overlapping peptides on the N terminal were shown to have strong signals while C terminal peptides were shown to have weak signals recognized by polyclonal pool sera. The mapped epitopes are set forth below:

| | | |
|---|---|---|
| E1(1-12) | MGSMQSLFDKIG | (SEQ ID NO: 1) |
| E2(7-18) | LFDKIGQLFVDA | (SEQ ID NO: 2) |
| E3(13-24) | QLFVDAFTEFLV | (SEQ ID NO: 3) |
| E4(19-30) | FTEFLVSIVDII | (SEQ ID NO: 4) |
| E5(25-36) | SIVDIIIFLAIL | (SEQ ID NO: 5) |
| E6(31-42) | IFLAILFGFTIA | (SEQ ID NO: 6) |
| E7(37-48) | FGFTIAGWLVVF | (SEQ ID NO: 7) |
| E8(43-54) | GWLVVFCIRLVC | (SEQ ID NO: 8) |
| E9(49-60) | CIRLVCSAILRT | (SEQ ID NO: 9) |
| E10(55-66) | SAILRTRPAIHS | (SEQ ID NO: 10) |
| E11(61-72) | RPAIHSEQLQKI | (SEQ ID NO: 11) |
| E12(cont) | G | (SEQ ID NO: 12) |

These results demonstrate that while the N terminal should be a strong antigenic site, the C terminal is a weak antigenic site. Immunized mice with the C terminal sequence of PRRSV strain SD-23983 of PRRSV generated a new 2b protein specific MAb, designed 17C3. When more overlapping peptides were tested and stained with the polyclonal field sera, three overlapping antigenic sequences E1, E2 and E3 located at the first 24 amino acid region were mapped (FIG. 1A-1B) (SEQ ID NOS:14-37).

Variations 2b Protein from Different Strain of PRRSV

As the locations of 2b B cell epitope have been mapped, the serological properties and cross-reactivity of these 2b epitopes were next investigated. According to the sequence analysis on over sixty different North American PRRSV strains, 2b have a nucleotide identity of 88 to 100% and amino acid identity of 81 to 100%. The optimal target sequence is "PAIHPEQL" (SEQ ID NO:13) for the 2b C terminal MAb 17C3. Cross-reactivity of 17C3 on different strain of PRSSV (SD23983, VR2332, MLV, JA142 and ATP) with minor changes in the C terminal of 2b was addressed by immunoprecipitation/Western immunoblot assay. The results showed that only 2b derived from SD23983-infected MARC-145 cell lysates can be detected. Thus, minor variations in the 17C3 epitope region significantly affects the antibody binding.

Figure 2:
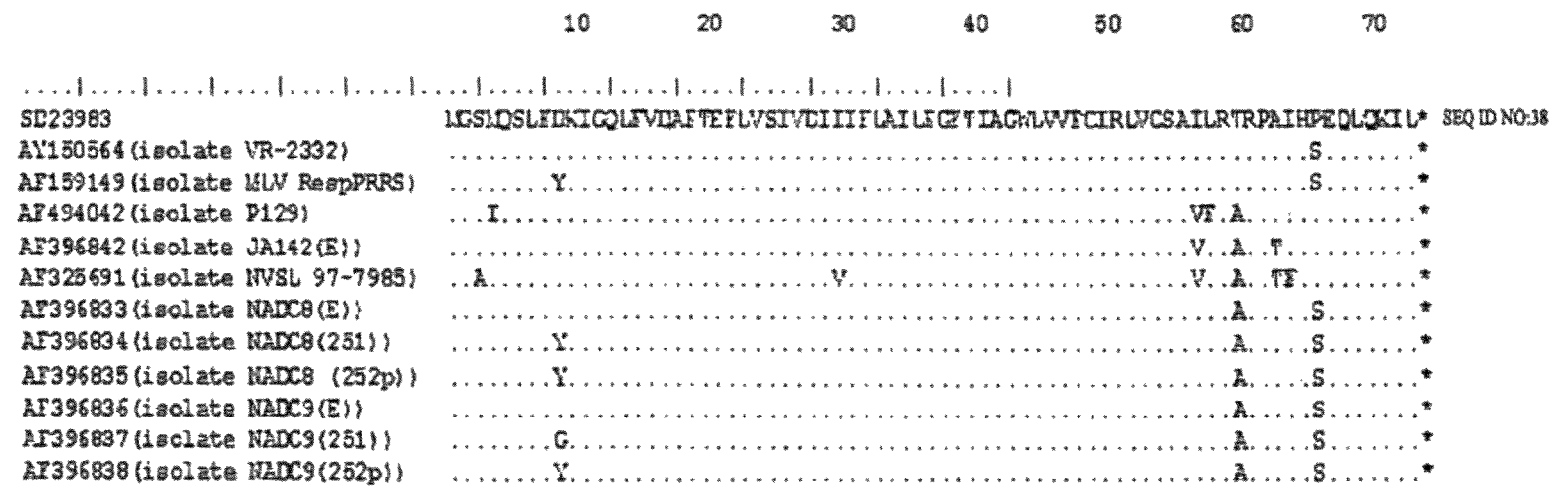

The antigenicity of 2b on different strains of PRRSV (SD23983, VR2332, MLV, JA142 and ATP) by using polyclonal anti-PRRSV pig serum that can detect 2b of SD23983 was next examined. Western Immunoblot analysis showed that 2b infected MARC-145 cell lysates of SD23983, VR2332, JA142 and ATP were detected while MLV respPRRS-infected MARC-145 cell lysates showed no detection. (FIG. 2) (SEQ ID NO:38). Since MLV and VR2332 only have one amino acid difference at the $9^{th}$ position on the N terminal of 2b, these results implied that the N terminal of 2b should contain the immunodominant epitope. Large quantities of a 15 kDa and slightly faster migrating N proteins were also detected which showed that the lane contained even more loading of MLV specific proteins when compare to lanes that contain 23983, JA142 and ATP as well as VR2332 viral specific proteins. Therefore, it is not because there is less loading of MLV protein onto the SDS-PAGE gel. The two forms of N protein have been reported before when using performing immunoprecipitation using anti-N Mabs (Nelson, et al., 1993). Therefore the preliminary results showed that the N terminal of 2b does not cross-react between MLV respPRRSV and other commonly known isolates.

Figure 3:
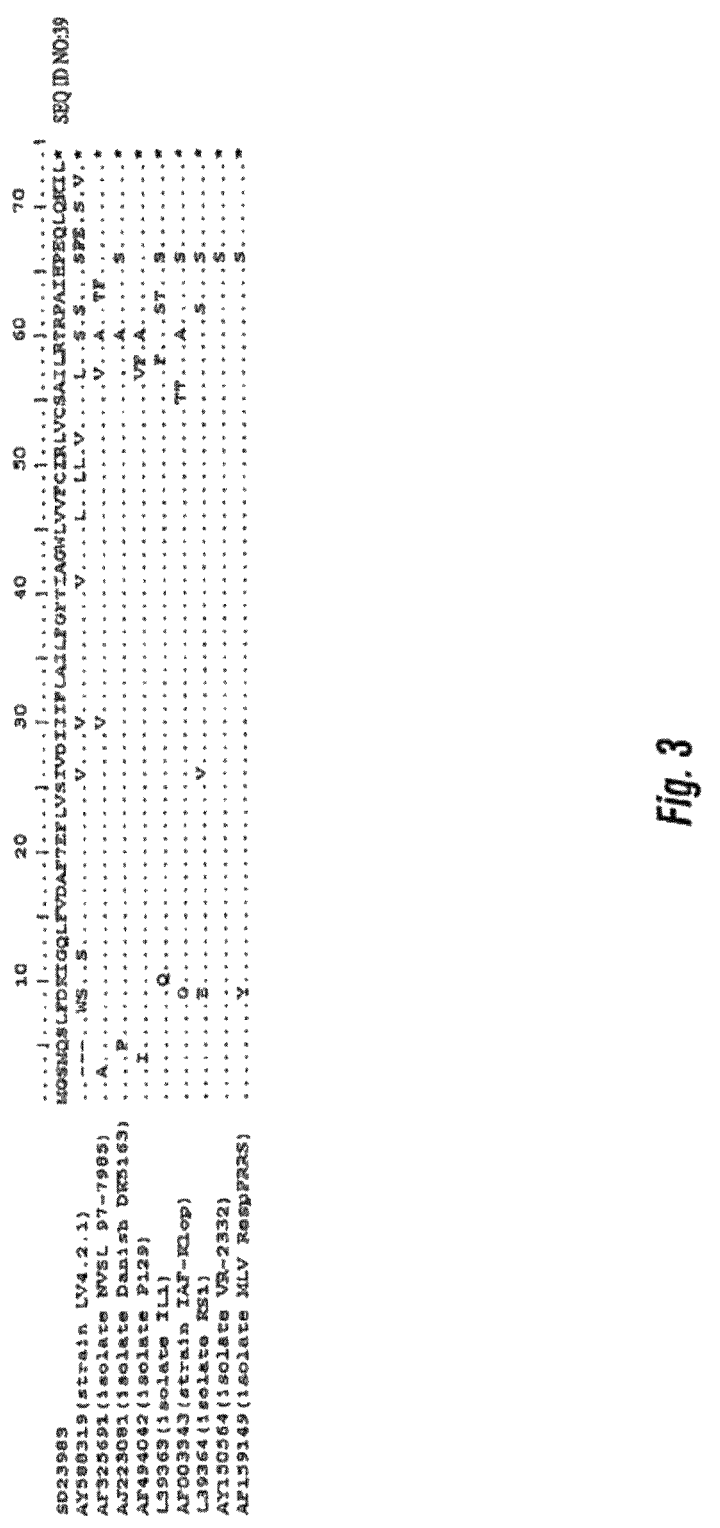

As mentioned above, sequence analysis of 2b between the parental strain VR2332 and the attenuated strain MLV respPRRSV showed that there is only one amino acid change (D9Y) in the N terminal region of 2b. Since 2b have been shown to be an essential protein in PRRSV replication, it is unlikely that 2b is not expressed in MLV respPRRS-infected cells. In order to rule out the possibility that 2b is not present in MLV respPRRS-infected MARC-145 cells and are thus undetected, short peptides that cover the first 20 amino acids of different 2b proteins were generated by fusion with GST tag. The results showed that all truncated GST2b fusion proteins derived from MLV respPRRS (D9Y), VR2332 (D9), KS1 (D9E), IAF-KLOP (D9G) and GST alone can be detected by the anti-GST antibody. (FIG. 3) (SEQ ID NO:39). GST2b fusion peptides are different in size when compare to the GST alone control (GSTΔEcoRI). The GST control is customized to contain the translation stop codon right after the end of the GST coding region by cutting at the EcoRI site and end finding with blunt end re-ligation of the pGEX6P3 vector. The GST only control thus would not carry extra-amino acids that may increase its molecular weight. This provides perfect control for 2b N terminal inserts which inserted at the EcoRI and Xho I site of pGEX6P3. When staining with the anti-PRRSV pig serum that can detect 2b from SD23983, only truncated 2b peptide derived from VR2332 can be detected (FIG. 6) and not other truncated 2b with different residues substitution at the ninth amino acid position. On the other hand, when staining with polyclonal anti-PRRSV serum, 2b cross-reactivity can be observed with PRRSV strains that have their 2b protein different from that of SD23983 with similar properties residues (M4I) at position 4. (FIG. 3) (SEQ ID NO:39). Further, inclusion of other 2b sequence from PRRSV strain found in GenBank showed that changes in position 3 (NVSL 97-7985) also does not affect the cross-reactivity. (FIG. 3) (SEQ. NO:39). However, changes in 9 and 10 amino acid do affect the cross-reactivity. Therefore, the limiting factor for the cross-reactivity VR2332 and other isolates should be at the position 9 and 10 amino acids. It is likely that other amino acids on the N terminal are also important for the binding of antibodies, but they are more conserved and should not affect cross-reactivity.

Passage of MLV-Like PRRSV Strain in Pigs

Figure 6:
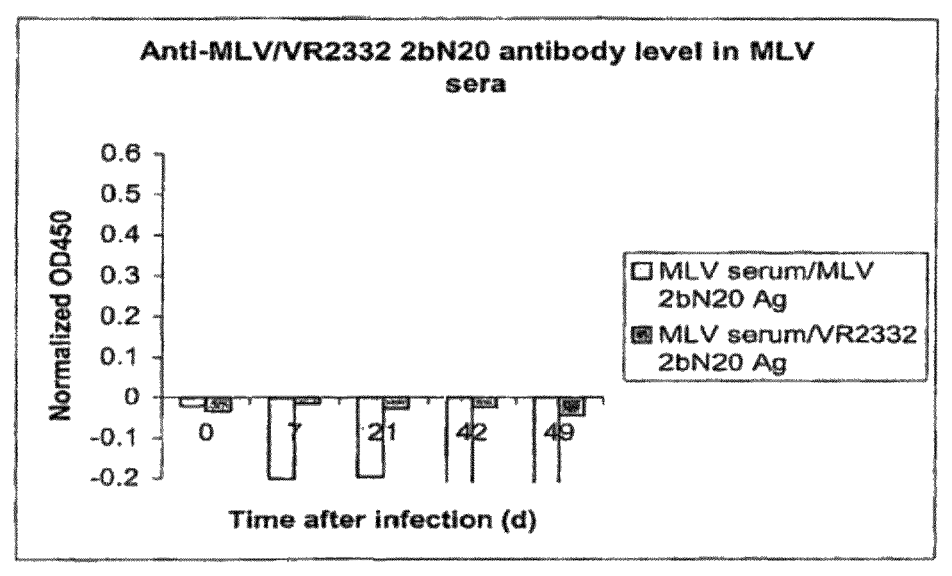

According to 2b sequence analysis and the results from the Western blot assay, MLV or PRRSV strains that have been passage in MARC-145 cells for many generation such as NADC8/251 might gain a "D9Y" phenotype (FIG. 2) (SEQ ID NO. 38). Serum collected from the parental strain VR2332 would not cross-react with the 2b sequence from MLV. In fact, 2b N terminal of MLV 2b peptide did not seem to be immunogenic or antigenic since serum collected from both MLV vaccinated and VR2332-infected animals fail to detect it when tested with Western blot and ELISA assay (FIG. 6). Since there is no cross-reactivity between MLV and VR2332 at the 2b N terminal region, therefore it seem to be a good candidate for the setup of serological differential assay for the differentiation between vaccinated and natural infected animals. 2b Sequence retrieved Genbank showed that more than 80% of the PRRSV strains have an N terminal identical or similar to VR2332, thus the corresponding anti-2b N terminal antibodies can be detected simply with VR2332 2b N terminal sequence as detection antigen (FIG. 4)(SEQ ID NOS. 39-40). Further studies is needed to investigate whether other 2b sequence from field isolates are antigenic and cross-reactive with the 2b N terminal antigen of VR2332. Cross-reactivity among field isolates at the 2b N terminal region, can certainly help to cut down the cost on the synthesis of multiple detection antigens.

Figure 5B:
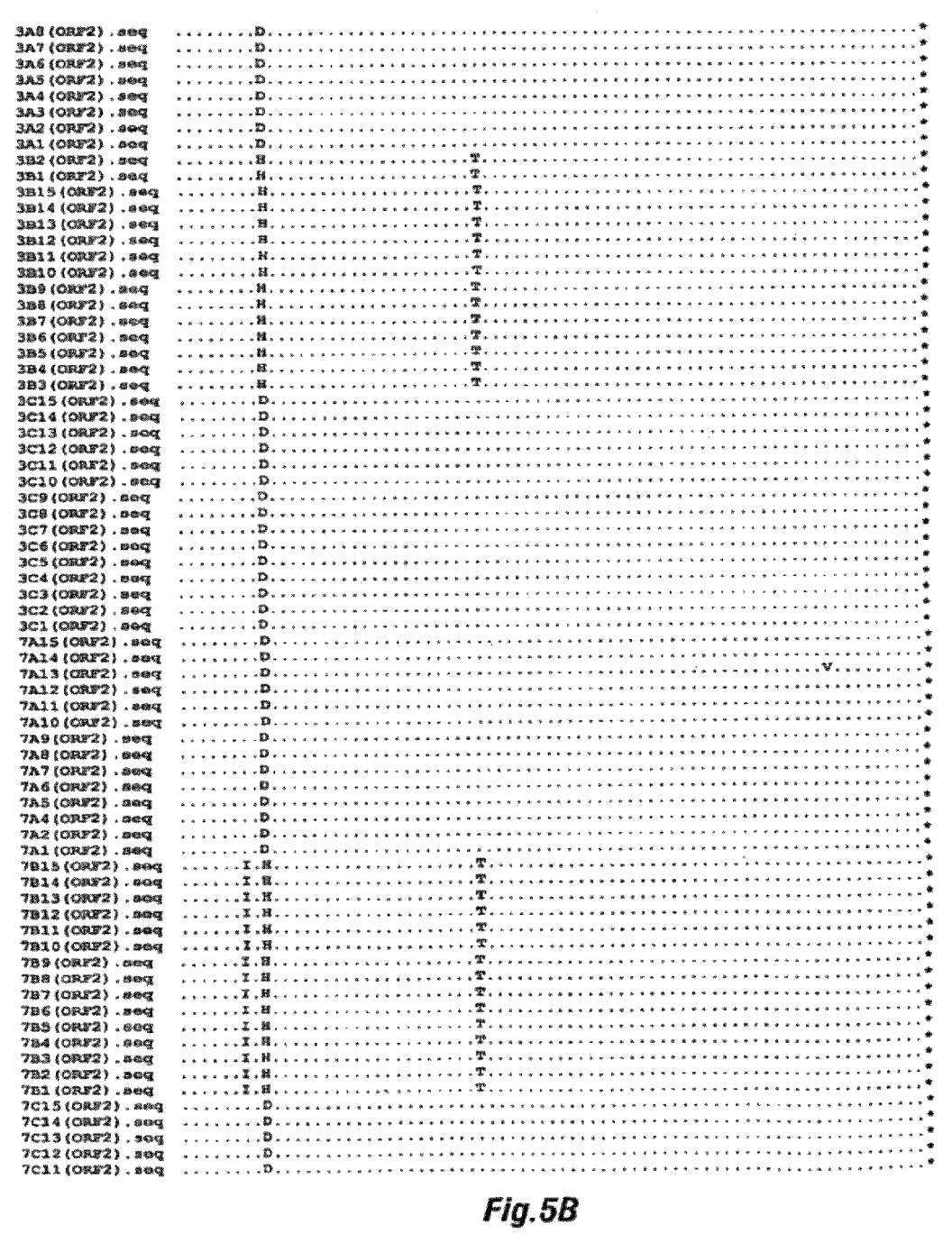
Figure 5C:
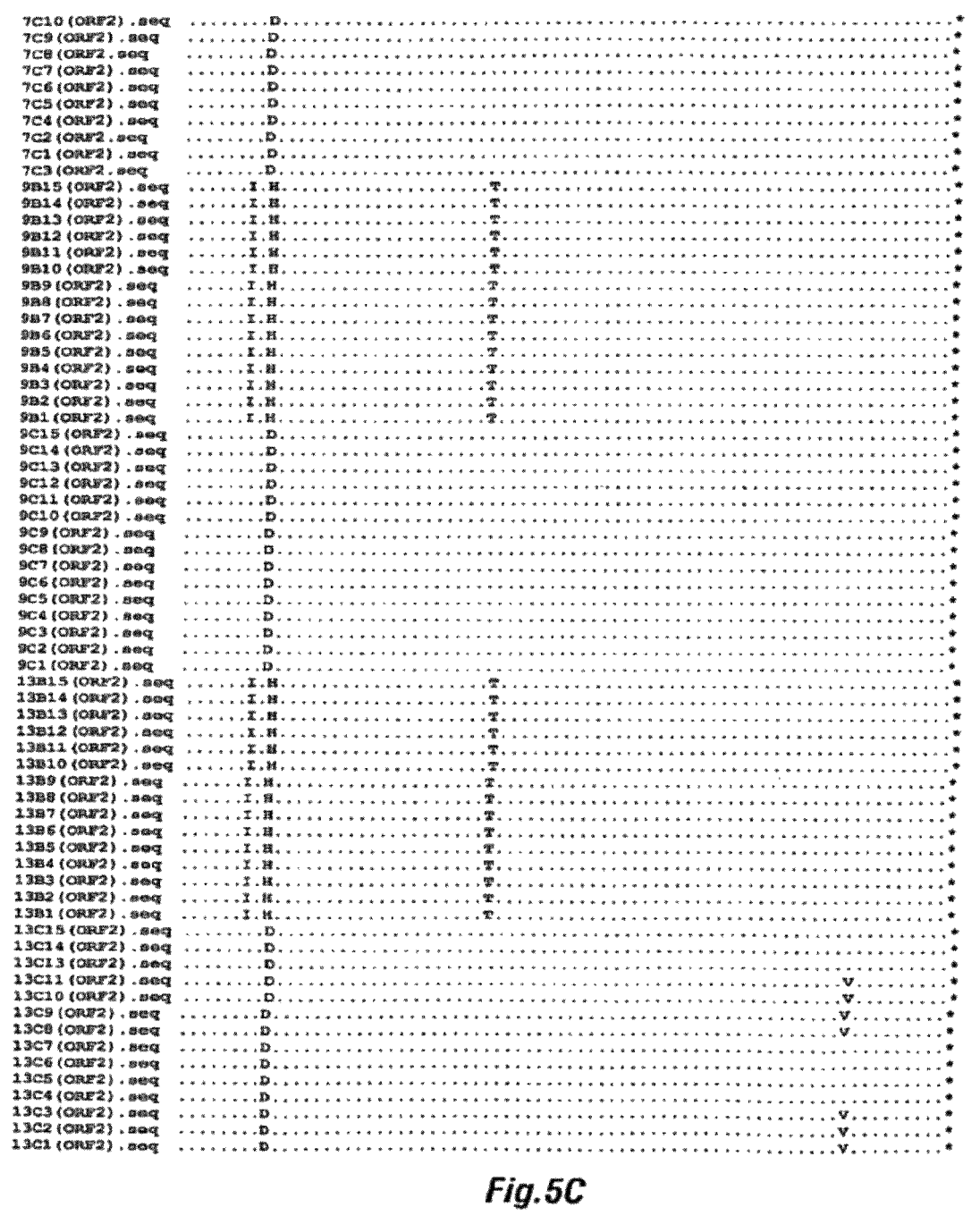
Figure 8:
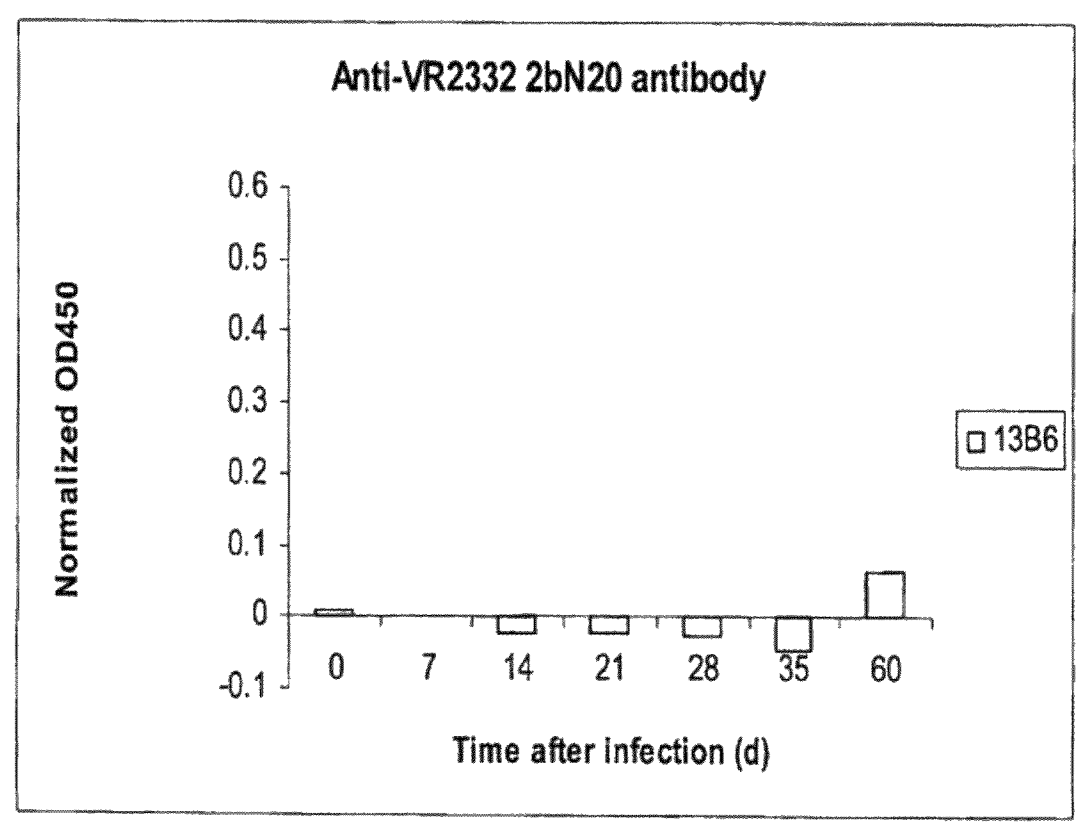

Besides the cross-reactivity issue, another important issue is the stability of the MLV 2b N terminal sequence in pigs. Since mutation of PRRSV in the same host can happen, it is necessary to confirm how stable the D9Y phenotype maintained in pigs as well as the humoral immune response follow infection or immunization. Changing of the D9Y mutation back to sequence in pigs, which is antigenic or identical to 2b N terminal sequence in VR2332 within one in vivo passage, would significantly affect this 2b differentiation assay. To test this possibility, the 2b region of viruses that have been collected from previous in vivo serial passage experiments was analyzed. The in vivo passage experiment represented pig to pig passage and without in vitro passage of MARC-145 cell culture in between. According to sequence analysis, pigs infected with a virus called CC-01, have the 2b "D9Y" phenotype maintained up to the second passage in pigs. However, by the third in vivo passage, the "D9Y" phenotype disappears and viruses either re-gain the parental 2b phenotype as seen in the line C in vivo passages (3C) or change to other phenotype (L to I and Y to H changes at position 7 and 9 respectively) in the line B passages (3B) (FIG. 5) (SEQ ID NO:39). The L7I and Y9H in the line 3B still can be detected at the thirteen passages, the 13B. One of the isolates in the 13B passages, the 13B6, was test for its antigenicity and the cross-reactivity to VR2332. The 2b N terminal of 13B6 is antigenic and can be detected either with the VR2332 and JA142 serum. However, 13B6 serum (60 dpi pool serum) fails to detect its own 2b N terminal peptide in the Western blot assay while picking up a VR2332 2b N terminal peptide signal in an ELISA assay (FIG. 8). These Western blot and ELISA assay results show there is a two-way cross-reactivity between VR2332 and 13B6 at a later point of infection.

Detection of Anti-2b N Terminal Sequence with Indirect ELISA Assay

As noted above, VR2332, 13C8 and 13B6 serum samples recognized VR2332 2b N terminal antigen. The earlier time to detect significant increase (0.001 at 0 dpi vs 0.09 at 21 dpi; p<0.05) in the normalized average antibodies level to VR2332 2b N terminal antigen by an indirect ELISA assay with VR2332 serum is around 21 dpi while MLV 2b N terminal remain undetected either by serum samples from the anti-VR2332 or anti-MLV serum panels. Some ELISA assays have a higher level of antibodies on the 0 dpi serum samples. This may be due to non-specific maternal antibodies since the levels drop when detected at 7 dpi (FIG. 6). The normalized OD450 anti-VR2332 2b N terminal antibody level detected by VR2332 serum samples is approximately 0.12 and 0.43 at 28 dpi and 49 dpi, respectively. 13C8, one of the isolates from the thirteenth in vivo line C passage of strain CC-01, also has the same 2b N terminal as VR2332 showed to have a significantly higher average normalized anti-VR2332 2b N terminal antibodies level as early as 35 dpi (0.34 at 35 dpi vs 0.01 at 28 dpi; p<0.05) and reach a normalized OD of 0.52 at 60 dpi (FIGS. 7A-7D). According to the sequencing analysis of strain 13B6, another thirteenth in vivo passage of CC01 but on line B, the 2b N terminal region change to sequence different from VR2332 and MLV. As previously noted, this new 2b N terminal sequence has also been shown to be antigenic and can be detected with anti-VR2332 pool serum. However, 13B6-infected pigs only induce a slightly distinguishable antibody signals to the 13B6 and VR2332 2b N terminal sequence when compared to MLV 2b in a Western blot assay. When detected with indirect ELISA assay, 13B6 sera have weak but detectable level of anti-VR2332 2b N terminal signals (average normalized OD450=0.064) on 60 dpi samples when compare to samples collected between 7 to 35 dpi.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence, which is effective to meet the objectives there intended, unless the context specifically indicates to the contrary.

All articles cited herein and in the following list are hereby expressly incorporated in their entirety by reference.

CITATIONS

1. Allende, R., T. L. Lewis, Z. Lu, D. L. Rock, G. F. Kutish, A. Ali, A. R. Doster, and F. A. Osorio. 1999. North American and European porcine reproductive and respiratory syndrome viruses differ in non-structural protein coding regions. J. Gen. Virol. 80:307-315.
2. Bachmann, M. H., C. Mathiason-Dubard, G. H. Learn, A. G. Rodrigo, D. L. Sodora, P. Mazzetti, E. A. Hoover, and J. L. Mullins, 1997. Genetic diversity of feline immunodeficiency virus: dual infection, recombination, and distinct evolutionary rates among envelope sequence clades. J. Virol. 71:4241-4253.
3. Berinstein, A., H. S. Sellers, D. J. King, and B. S. Seal. 2001. Use of a heteroduplex mobility assay to detect differences in the fusion protein cleavage site coding sequence among Newcastle disease virus isolates. J. Clin. Microbiol. 39:3171-3178.
4. Botner, A., Bo. Strandbygaard, K. J. Sorensen, P. Have, K. G. Madsen, E. S. Madsen, and S. Alexandersen. 1997. Appearance of acute PPRS-like symptoms in sow herds after vaccination with a modified live PRRS vaccine. Vet. Rec. 141:497-499.
5. Chezzi, C., and B. D. Schoub. 1996. Differntiation between vaccine-related and wild-type polioviruses with a heteroduplex mobility assay. J. Virol. Methods 62:93-102.
6. Delwart, E. L., E. G. Shpaer, J. Louwagie, F. E. McCutchan, M. Grez, H. Rubsamen-Waigmann, and J. I. Mullins. 1993. Genetic relationships determined by a DNA heteroduplex mobility assay: analysis of HIV-1 env genes. Science 262:1257-1261.
7. Gretch, D. R., S. J. Polyak, J. J. Wilson, R. L. Carithers, Jr., J. D. Perkins, and L. Corey. 1996. Tracking hepatitis C virus quasispecies major and minor variants in symptomatic and asymptomatic liver transplant recipients. J. Virol. 70:7622-7631.
8. Kapur, V., M. R. Elam, T. M. Pawlovich, and M. P. Murtaugh. 1996. Genetic variation in porcine reproductive and respiratory syndrome virus isolates in the Midwestern United States. J. Gen. Virol. 77:1271-1276.
9. Key, K. F., G. Haqshenas, D. K. Guenette, S. L. Swenson, T. E. Toth, and X. J. Meng. 2001. Genetic variation and phylogenetic analyses of the ORF5 gene of acute porcine reproductive and respiratory syndrome virus isolates. Vet. Microbiol. 83:249-263.
10. Kreis, S., and T. Whistler. 1997. Rapid identification of measles virus strains by the heteroduplex mobility assay. Virus Res. 47:197-203.
11. Mardassi, H., R. Athanassiuous, S. Mounir, and S. Dea. 1994. Porcine reproductive and respiratory syndrome virus; morphological, biochemical and serological characteristics of Quebec isolates associated with acute and chronic outbreadks of porcine reproductive and respoiratory syndrome. Can. J. Vet. Res. 58:55-64.
12. Meng, X. J., P. S. Paul, and P. G. Halbur. 1994. Molecular cloning and nucleotide sequencing of the 3'-terminal genomic RNA of the porcine reproductive and respiratory syndrome virus. J. Gen. Virol. 75:1795-1801.
13. Meng, X. J., P. S. Paul, P. G. Halbur, and M. A. Lum. 1995a. Phylogenetic analyses of the putative M (ORF 6) and N (ORF 7) genes of porcine reproductive and respiratory syndrome virus (PRRSV): implication for the existence of two genotypes of PRRSV in the USA and Europe. Arch. Virol. 140:745-755.
14. Meng, X. J., P. S. Paul, P. G. Halbur, and I. Morozov. 1995b. Sequence comparison of open reading frames 2 to 5 of low and high virulence United States isolates of porcine reproductive and respiratory syndrome virus. J. Gen. Virol. 76:3181-3188.
15. Meng, X. J., P. S. Paul, I. Morozov, and P. G. Halbur. 1996. A nested set of six or seven subgenomic mRNAs is formed in cells infected with different isolates of porcine reproductive and respiratory syndrome virus. J. Gen. Virol. 77:1265-1270.
16. Meng, X. J. 2000. Heterogeneity of porcine reproductive and respoiratory syndrome virus; implications for current vaccine efficacy and future vaccine development. Vet. Microbiol. 74:309-329.
17. Mengeling, W. L., K. M. Lager, and A. C. Vorwald. 1999. Safety and efficacy of vaccination of pregnant gilts against porcine reproductive and respiratory syndrome. Am. J. Vet. Res. 60:796-801.
18. Mengeling, J. J., M. M. Hulst, E. J. De Meijer, P. L. Moonen, A. Den Besten, E. P. De Kluyver, G. Wensvoort, and R. J. Moormann. 1999. Idnetification and clinical assessment of suspected vaccine-related field strains of porcine reproductive and respiratory syndrome virus. Am. J Vet Res. 60:334-340.
19. Meulenberg, J. J., M. M. Hulst, E. J. De Meijer, P. L. Moonen, A. Den Besten, E. P. De Kluyver, G. Wensvoort, and R. J. Moormann. 1993. Lelystad virus, the causative agent of porcine epidemic abortion and respiratory syndrome (PEARS), is related to LDV and EAV. Virology 192:62-72.
20. Murtaugh, M. P., K. S. Faaberg, J. Laber, M. Elam, and V. Kapur. 1998.

21. Nelsen, C. J., M. P. Murtaugh, and K. S. Faaberg. 1999. Porcine reproductive and respiratory syndrome virus comparison: divergent evolution on two continents. J. Virol. 73:270-280.
22. Oleksiewicz, M. B., A. Botner, K. G. Madsen, and T. Storgaard. 1998. Sensitive detection and typing of porcine reproductive and respiratory syndrome virus by RT-PCR amplification of whole viral genes. Vet. Microbiol. 64:7-22.
23. Opriessnig, T., P. G. Halbur, K. J. Yoon, R. M. Pogranichniy, K. M. Harmon, R. Evans, K. F. Key, F. J. Pallares, P. Thomas, and X. J. Meng. 2002. Comparative pathogenicity of a modified live PRRSV vaccine (Ingelvac PRRS MLV), the parent strain of the vaccine (ATCC VR2332), ATCC VR 2385, and two recent field isolates of PRRSV. J. Virol. 76:11837-11844.
24. Osorio, F. A., F. Zuckermann, R. Wills, W. Meier, S. Christian, J. Galeota, and A. Doster. 1998. PRRSV: comparison of commercial vaccines in their ability to induce protection against current PRRSV strains of high virulence. 1998 Allen D. Leman Swine Conf. 25:176-182.
25. Polson, D. D., W. E. Marsh, and G. D. Dial. 1992. Financial evaluation and decision making in the swine breeding herd. Vet. Clin. North Am. Food Anim. Pract. 8:725-747.
26. Storgaard, T., M. Oleksiewicz, and A. Botner. 1999. Examination of the selective pressures on a live PRRS vaccine virus. Arch. Virol. 144:2389-2401.
27. Wesley, R. D., W. L. Mengeling, K. M. Lager, A. C. Vorwald, and M. B. Roof 1999. Evidence for divergence of restriction fragment length polymorphism patterns following in vivo replication of porcine reproductive and respiratory syndrome virus. Am. J. Vet. Res. 60:463-467.
28. Wilson, J. J., S. J. Polyak, T. D. Day, and D. R. Gretch. 1995. Characterization of simple and complex hepatitis C virus quasispecies by heterduplex gel shift analysis: correlation with nucleotide sequencing. J. Gen. Virol. 76:1763-1771.
29. Zou, S. 1997. A practical approach to genetic screening for influenza virus variants. J. Clin. Microbiol. 35:2623-2627.

What is claimed is:

1. A method of determining whether a pig has received a commercial PRRSV modified live attenuated vaccine (MLV) comprising:
   a. obtaining a biological sample from an individual;
   b. contacting the biological sample with an antibody that binds to the N terminal region of the 2b protein of PRRSV to form a complex when there is an aspartic acid at position 9; wherein the position number of said PRRSV corresponds to the position number in SEQ ID NO:40; and
   c. assaying for the presence of said complex, wherein an aspartic acid at position 9 indicates that said pig has not received a commercial PRRSV modified live attenuated vaccine (MLV) and a tyrosine or glycine at said position indicates that said pig has received said MLV.

2. The method of claim 1 wherein the PRRSV is free or bound to a carrier molecule or solid support.

3. The method of claim 1 wherein the antibody is selected from the group consisting of a polyclonal antibody and a monoclonal antibody.

4. The method of claim 1 wherein the biological sample is selected from the group consisting of urine, whole blood, plasma, serum, saliva, semen, stool, sputum, cerebral spinal fluid, tears, mucus, tissue, and tissue extract.

5. The method of claim 1 wherein the antibody is linked to or incorporates a label.

6. The method of claim 1 wherein the assaying step uses an immunoassay selected from the group consisting of EMIT, radio immunoassay, fluorescent immunoassay, enzyme channeling techniques, and ELISA.

7. The method of claim 1 wherein the assaying step uses ELISA-based immunoenzymatic detection.

8. A method of determining whether a pig has received a commercial PRRSV modified live attenuated vaccine (MLV) in a biological sample comprising:
   a. contacting the biological sample with an antibody or fragment thereof that binds to the N terminal region of the 2b protein of PRRSV to form a complex when there is an aspartic acid at position 9 corresponding to position 9 of SEQ ID NO:40;

b. assaying for the presence of said complex; and
c. determining the amino acid present at position 9 of the 2b protein of PRRSV in said sample, wherein an aspartic acid at position 9 indicates that a pig has not received a commercial PRRSV Modified live attenuated vaccine (MLV) and a tyrosine or glycine at said position indicates that said pig has received said commercial PRRSV modified live attenuated vaccine (MLV).

9. The method of claim 8 wherein the antibody or fragment thereof is a polyclonal antibody.

* * * * *

SEQUENCE LISTING

<160> NUMBER OF SEQ ID NOS: 40

<210> SEQ ID NO 1
<211> LENGTH: 12
<212> TYPE: PRT
<213> ORGANISM: Porcine Reproductive and Respiratroy Syndrome Virus

<400> SEQUENCE: 1

Met Gly Ser Met Gln Ser Leu Phe Asp Lys Ile Gly
1               5                   10

<210> SEQ ID NO 2
<211> LENGTH: 12
<212> TYPE: PRT
<213> ORGANISM: Porcine Reproductive and Respiratroy Syndrome Virus

<400> SEQUENCE: 2

Leu Phe Asp Lys Ile Gly Gln Leu Phe Val Asp Ala
1               5                   10

<210> SEQ ID NO 3
<211> LENGTH: 12
<212> TYPE: PRT
<213> ORGANISM: Porcine Reproductive and Respiratroy Syndrome Virus

<400> SEQUENCE: 3

Gln Leu Phe Val Asp Ala Phe Thr Glu Phe Leu Val
1               5                   10

<210> SEQ ID NO 4
<211> LENGTH: 12
<212> TYPE: PRT
<213> ORGANISM: Porcine Reproductive and Respiratroy Syndrome Virus

<400> SEQUENCE: 4

Phe Thr Glu Phe Leu Val Ser Ile Val Asp Ile Ile
1               5                   10

<210> SEQ ID NO 5
<211> LENGTH: 12
<212> TYPE: PRT
<213> ORGANISM: Porcine Reproductive and Respiratroy Syndrome Virus

```
<400> SEQUENCE: 5

Ser Ile Val Asp Ile Ile Phe Leu Ala Ile Leu
1               5                   10

<210> SEQ ID NO 6
<211> LENGTH: 12
<212> TYPE: PRT
<213> ORGANISM: Porcine Reproductive and Respiratroy Syndrome Virus

<400> SEQUENCE: 6

Ile Phe Leu Ala Ile Leu Phe Gly Phe Thr Ile Ala
1               5                   10

<210> SEQ ID NO 7
<211> LENGTH: 12
<212> TYPE: PRT
<213> ORGANISM: Porcine Reproductive and Respiratroy Syndrome Virus

<400> SEQUENCE: 7

Phe Gly Phe Thr Ile Ala Gly Trp Leu Val Val Phe
1               5                   10

<210> SEQ ID NO 8
<211> LENGTH: 12
<212> TYPE: PRT
<213> ORGANISM: Porcine Reproductive and Respiratroy Syndrome Virus

<400> SEQUENCE: 8

Gly Trp Leu Val Val Phe Cys Ile Arg Leu Val Cys
1               5                   10

<210> SEQ ID NO 9
<211> LENGTH: 12
<212> TYPE: PRT
<213> ORGANISM: Porcine Reproductive and Respiratroy Syndrome Virus

<400> SEQUENCE: 9

Cys Ile Arg Leu Val Cys Ser Ala Ile Leu Arg Thr
1               5                   10

<210> SEQ ID NO 10
<211> LENGTH: 12
<212> TYPE: PRT
<213> ORGANISM: Porcine Reproductive and Respiratroy Syndrome Virus

<400> SEQUENCE: 10

Ser Ala Ile Leu Arg Thr Arg Pro Ala Ile His Ser
1               5                   10

<210> SEQ ID NO 11
<211> LENGTH: 12
<212> TYPE: PRT
<213> ORGANISM: Porcine Reproductive and Respiratroy Syndrome Virus

<400> SEQUENCE: 11

Arg Pro Ala Ile His Ser Glu Gln Leu Gln Lys Ile
1               5                   10

<210> SEQ ID NO 12
<211> LENGTH: 133
<212> TYPE: PRT
<213> ORGANISM: Porcine Reproductive and Respiratroy Syndrome Virus

<400> SEQUENCE: 12

Met Gly Ser Met Gln Ser Leu Phe Asp Lys Ile Gly Leu Phe Asp Lys
```

```
                 1               5                  10                 15
Ile Gly Gln Leu Phe Val Asp Ala Gln Leu Phe Val Asp Ala Phe Thr
             20                 25                 30

Glu Phe Leu Val Phe Thr Glu Phe Leu Val Ser Ile Val Asp Ile Ile
             35                 40                 45

Ser Ile Val Asp Ile Ile Ile Phe Leu Ala Ile Leu Ile Phe Leu Ala
             50                 55                 60

Ile Leu Phe Gly Phe Thr Ile Ala Phe Gly Phe Thr Ile Ala Gly Trp
 65                 70                 75                 80

Leu Val Val Phe Gly Trp Leu Val Val Phe Cys Ile Arg Leu Val Cys
                 85                 90                 95

Cys Ile Arg Leu Val Cys Ser Ala Ile Leu Arg Thr Ser Ala Ile Leu
             100                105                110

Arg Thr Arg Pro Ala Ile His Ser Arg Pro Ala Ile His Ser Glu Gln
             115                120                125

Leu Gln Lys Ile Gly
         130

<210> SEQ ID NO 13
<211> LENGTH: 8
<212> TYPE: PRT
<213> ORGANISM: Porcine Reproductive and Respiratroy Syndrome Virus

<400> SEQUENCE: 13

Pro Ala Ile His Pro Glu Gln Leu
1               5

<210> SEQ ID NO 14
<211> LENGTH: 12
<212> TYPE: PRT
<213> ORGANISM: Porcine Reproductive and Respiratroy Syndrome Virus

<400> SEQUENCE: 14

Met Gly Ser Met Gln Ser Leu Phe Asp Lys Ile Gly
1               5                   10

<210> SEQ ID NO 15
<211> LENGTH: 11
<212> TYPE: PRT
<213> ORGANISM: Porcine Reproductive and Respiratroy Syndrome Virus

<400> SEQUENCE: 15

Gly Ser Met Gln Ser Leu Phe Asp Lys Ile Gly
1               5                   10

<210> SEQ ID NO 16
<211> LENGTH: 10
<212> TYPE: PRT
<213> ORGANISM: Porcine Reproductive and Respiratroy Syndrome Virus

<400> SEQUENCE: 16

Ser Met Gln Ser Leu Phe Asp Lys Ile Gly
1               5                   10

<210> SEQ ID NO 17
<211> LENGTH: 9
<212> TYPE: PRT
<213> ORGANISM: Porcine Reproductive and Respiratroy Syndrome Virus

<400> SEQUENCE: 17

Met Gln Ser Leu Phe Asp Lys Ile Gly
1               5
```

```
<210> SEQ ID NO 18
<211> LENGTH: 8
<212> TYPE: PRT
<213> ORGANISM: Porcine Reproductive and Respiratroy Syndrome Virus

<400> SEQUENCE: 18

Gln Ser Leu Phe Asp Lys Ile Gly
1               5

<210> SEQ ID NO 19
<211> LENGTH: 7
<212> TYPE: PRT
<213> ORGANISM: Porcine Reproductive and Respiratroy Syndrome Virus

<400> SEQUENCE: 19

Ser Leu Phe Asp Lys Ile Gly
1               5

<210> SEQ ID NO 20
<211> LENGTH: 12
<212> TYPE: PRT
<213> ORGANISM: Porcine Reproductive and Respiratroy Syndrome Virus

<400> SEQUENCE: 20

Leu Phe Asp Lys Ile Gly Gln Leu Phe Val Asp Ala
1               5                   10

<210> SEQ ID NO 21
<211> LENGTH: 11
<212> TYPE: PRT
<213> ORGANISM: Porcine Reproductive and Respiratroy Syndrome Virus

<400> SEQUENCE: 21

Leu Phe Asp Lys Ile Gly Gln Leu Phe Val Asp
1               5                   10

<210> SEQ ID NO 22
<211> LENGTH: 10
<212> TYPE: PRT
<213> ORGANISM: Porcine Reproductive and Respiratroy Syndrome Virus

<400> SEQUENCE: 22

Leu Phe Asp Lys Ile Gly Gln Leu Phe Val
1               5                   10

<210> SEQ ID NO 23
<211> LENGTH: 9
<212> TYPE: PRT
<213> ORGANISM: Porcine Reproductive and Respiratroy Syndrome Virus

<400> SEQUENCE: 23

Leu Phe Asp Lys Ile Gly Gln Leu Phe
1               5

<210> SEQ ID NO 24
<211> LENGTH: 8
<212> TYPE: PRT
<213> ORGANISM: Porcine Reproductive and Respiratroy Syndrome Virus

<400> SEQUENCE: 24

Leu Phe Asp Lys Ile Gly Gln Leu
1               5

<210> SEQ ID NO 25
```

```
<211> LENGTH: 7
<212> TYPE: PRT
<213> ORGANISM: Porcine Reproductive and Respiratroy Syndrome Virus

<400> SEQUENCE: 25

Leu Phe Asp Lys Ile Gly Gln
1               5

<210> SEQ ID NO 26
<211> LENGTH: 11
<212> TYPE: PRT
<213> ORGANISM: Porcine Reproductive and Respiratroy Syndrome Virus

<400> SEQUENCE: 26

Phe Asp Lys Ile Gly Gln Leu Phe Val Asp Ala
1               5                   10

<210> SEQ ID NO 27
<211> LENGTH: 10
<212> TYPE: PRT
<213> ORGANISM: Porcine Reproductive and Respiratroy Syndrome Virus

<400> SEQUENCE: 27

Asp Lys Ile Gly Gln Leu Phe Val Asp Ala
1               5                   10

<210> SEQ ID NO 28
<211> LENGTH: 9
<212> TYPE: PRT
<213> ORGANISM: Porcine Reproductive and Respiratroy Syndrome Virus

<400> SEQUENCE: 28

Lys Ile Gly Gln Leu Phe Val Asp Ala
1               5

<210> SEQ ID NO 29
<211> LENGTH: 8
<212> TYPE: PRT
<213> ORGANISM: Porcine Reproductive and Respiratroy Syndrome Virus

<400> SEQUENCE: 29

Ile Gly Gln Leu Phe Val Asp Ala
1               5

<210> SEQ ID NO 30
<211> LENGTH: 7
<212> TYPE: PRT
<213> ORGANISM: Porcine Reproductive and Respiratroy Syndrome Virus

<400> SEQUENCE: 30

Gly Gln Leu Phe Val Asp Ala
1               5

<210> SEQ ID NO 31
<211> LENGTH: 12
<212> TYPE: PRT
<213> ORGANISM: Porcine Reproductive and Respiratroy Syndrome Virus

<400> SEQUENCE: 31

Gln Leu Phe Val Asp Ala Phe Thr Glu Phe Leu Val
1               5                   10

<210> SEQ ID NO 32
<211> LENGTH: 11
<212> TYPE: PRT
<213> ORGANISM: Porcine Reproductive and Respiratroy Syndrome Virus
```

```
<400> SEQUENCE: 32

Gln Leu Phe Val Asp Ala Phe Thr Glu Phe Leu
1               5                   10

<210> SEQ ID NO 33
<211> LENGTH: 10
<212> TYPE: PRT
<213> ORGANISM: Porcine Reproductive and Respiratroy Syndrome Virus

<400> SEQUENCE: 33

Gln Leu Phe Val Asp Ala Phe Thr Glu Phe
1               5                   10

<210> SEQ ID NO 34
<211> LENGTH: 9
<212> TYPE: PRT
<213> ORGANISM: Porcine Reproductive and Respiratroy Syndrome Virus

<400> SEQUENCE: 34

Gln Leu Phe Val Asp Ala Phe Thr Glu
1               5

<210> SEQ ID NO 35
<211> LENGTH: 8
<212> TYPE: PRT
<213> ORGANISM: Porcine Reproductive and Respiratroy Syndrome Virus

<400> SEQUENCE: 35

Gln Leu Phe Val Asp Ala Phe Thr
1               5

<210> SEQ ID NO 36
<211> LENGTH: 7
<212> TYPE: PRT
<213> ORGANISM: Porcine Reproductive and Respiratroy Syndrome Virus

<400> SEQUENCE: 36

Gln Leu Phe Val Asp Ala Phe
1               5

<210> SEQ ID NO 37
<211> LENGTH: 24
<212> TYPE: PRT
<213> ORGANISM: Porcine Reproductive and Respiratroy Syndrome Virus

<400> SEQUENCE: 37

Met Gly Ser Met Gln Ser Leu Phe Asp Lys Ile Gly Gln Leu Phe Val
1               5                   10                  15

Asp Ala Phe Thr Glu Phe Leu Val
            20

<210> SEQ ID NO 38
<211> LENGTH: 73
<212> TYPE: PRT
<213> ORGANISM: Porcine Reproductive and Respiratroy Syndrome Virus

<400> SEQUENCE: 38

Met Gly Ser Met Gln Ser Leu Phe Asp Lys Ile Gly Gln Leu Phe Val
1               5                   10                  15

Asp Ala Phe Thr Glu Phe Leu Val Ser Ile Val Asp Ile Ile Ile Phe
            20                  25                  30

Leu Ala Ile Leu Phe Gly Phe Thr Ile Ala Gly Trp Leu Val Val Phe
        35                  40                  45
```

```
Cys Ile Arg Leu Val Cys Ser Ala Ile Leu Arg Thr Arg Pro Ala Ile
    50                  55                  60

His Pro Glu Gln Leu Gln Lys Ile Leu
65                  70

<210> SEQ ID NO 39
<211> LENGTH: 73
<212> TYPE: PRT
<213> ORGANISM: Porcine Reproductive and Respiratroy Syndrome Virus

<400> SEQUENCE: 39

Met Gly Ser Met Gln Ser Leu Phe Asp Lys Ile Gly Gln Leu Phe Val
1               5                   10                  15

Asp Ala Phe Thr Glu Phe Leu Val Ser Ile Val Asp Ile Ile Ile Phe
                20                  25                  30

Leu Ala Ile Leu Phe Gly Phe Thr Ile Ala Gly Trp Leu Val Val Phe
            35                  40                  45

Cys Ile Arg Leu Val Cys Ser Ala Ile Leu Arg Thr Arg Pro Ala Ile
    50                  55                  60

His Pro Glu Gln Leu Gln Lys Ile Leu
65                  70

<210> SEQ ID NO 40
<211> LENGTH: 69
<212> TYPE: PRT
<213> ORGANISM: Porcine Reproductive and Respiratroy Syndrome Virus

<400> SEQUENCE: 40

Met Gly Ser Met Gln Ser Leu Phe Asp Lys Ile Gly Gln Leu Phe Val
1               5                   10                  15

Asp Ala Phe Thr Glu Phe Leu Val Ser Ile Val Asp Ile Ile Ile Phe
                20                  25                  30

Leu Ala Ile Leu Phe Gly Phe Thr Ile Ala Gly Trp Leu Val Val Phe
            35                  40                  45

Cys Ile Arg Leu Val Cys Ser Ala Leu Arg Arg Pro Ala His Glu Gln
    50                  55                  60

Leu Gln Lys Ile Leu
65
```